US007829549B2

(12) United States Patent
Johnson

(10) Patent No.: US 7,829,549 B2
(45) Date of Patent: Nov. 9, 2010

(54) METHODS FOR TREATING BLEEDING DISORDERS USING SULFATED POLYSACCHARIDES

(75) Inventor: Kirk W. Johnson, Moraga, CA (US)

(73) Assignees: Baxter International Inc., Deerfield, IL (US); Baxter Healthcare S. A., Glattpark (Opfikon) (CH)

(*) Notice: Subject to any disclaimer, the term of this patent is extended or adjusted under 35 U.S.C. 154(b) by 0 days.

(21) Appl. No.: 12/386,026

(22) Filed: Apr. 13, 2009

(65) Prior Publication Data

US 2009/0269325 A1   Oct. 29, 2009

Related U.S. Application Data

(63) Continuation of application No. 11/140,504, filed on May 27, 2005, now Pat. No. 7,767,654.

(60) Provisional application No. 60/574,845, filed on May 27, 2004.

(51) Int. Cl.
 *A61K 31/715* (2006.01)
 *A61K 31/727* (2006.01)
 *A61K 31/70* (2006.01)
 *A01N 43/04* (2006.01)

(52) U.S. Cl. .................... 514/54; 514/56; 514/834; 514/23; 514/25

(58) Field of Classification Search ............... 514/54, 514/56, 834, 23, 25
See application file for complete search history.

(56) References Cited

U.S. PATENT DOCUMENTS

2003/0203845 A1   10/2003   Knudsen et al.

FOREIGN PATENT DOCUMENTS

| EP | 0251134A2 A | 1/1988 |
| JP | 2003 171262 A A | 6/2003 |
| WO | WO 99/18961 A1 A | 4/1999 |
| WO | WO 2004/029095 A | 4/2004 |

OTHER PUBLICATIONS

Kliem, V., Ringe, B., Barthels, M., Frei, U., Neumann, K.H. (1994) Successful renal transplantation in severe von Willebrand's disease. Nephrology Dialysis Transplantation, vol. 9, p. 837-838.*
Bates, et al., "The New Heparins," *Coron. Artery Dis.* 9(2-3):65-74 (1998).
Bishop, et al., "Recombinant Biologics For Treatment Of Bleeding Disorders," *Nat. Rev. Drug Discov.* 3(8):684-94 (2004).
Bourin, et al., "Glycosaminoglycans And The Regulation Of Blood Coagulation," *Biochem J.* 289(Pt 2):313-30 (1993).
Broze, "The Role Of Tissue Factor Pathway Inhibitor In A Revised Coagulation Cascade," *Semin. Haematol.* 29(3):159-69 (1992).
Broze, "The Rediscovery and Isolation Of TFPI," *J. Thromb. Haemost.* 1(8):1671-5 (2003).
Brummel, et al., "Factor Viia Replacement Therapy in Factor VII Deficiency," *J. Thromb. Haemost.* 2(10):1735-44 (2004).
Carcao, et al., "Prophylactic Factor Replacement in Hemophilia," *Blood Rev.* 18(2):101-13 (2004).
Church, et al., "Antithrombin Activity Of Fucoidan. The Interaction Of Fucoidan With Heparin Cofactor II, Antithrombin III, And Thrombin," *J. Biol. Chem.* 264(6):3618-23 (1989).
Colliec, et al., "Anticoagulant Prperties of a Fucoidan Fraction," *Thromb Res* 64:143-154 (1991).
Davie, et al., "The Coagulation Cascade: Initiation, Maintenance, And Regulation," *Biochemistry* 30(43):10363-70 (1991).
Erhardtsen, et al., "Blocking Of Tissue Factor Pathway Inhibitor (TFPI) Shortens The Bleeding Time In Rabbits With Antibody Induced Haemophilia A," *Blood Coagul. Fibrinolysis* 6(5):388-94 (1995).
Fryer, et al., "Selective O-Desulfation Produces Nonanticoagulant Heparin That Retains Pharmacological Activity In The Lung," *J Pharmacol Exp Ther.* 282(1):208-19 (1997).
Giedrojć, et al., "Comparative Study On The In Vitro And In Vivo Activities Of Heparinoids Derivative Investigated On The Animal Model," *J. Cardiovasc. Pharmacol.* 34(3):340-5 (1999).
Granert, et al., "Effects Of Polysaccharide Fucoidin On Cerebrospinal Fluid Interleukin-1 And Tumor Necrosis Factor Alpha In Pneumococcal Meningitis In The Rabbit," *Infect. Immun.* 67(5):2071-4 (1999).
Hirsh, et al., "New Anticoagulants," *Blood* 105(2):453-63 (2005).
Johnson, et al., "Novel Anticoagulants Based On Inhibition Of The Factor Viia/Tissue Factor Pathway," *Coron. Artery Dis.* 9(2-3):83-7 (1998).
Kleesiek, et al., "The 536C—>T Transition In The Human Tissue Factor Pathway Inhibitor (TFPI) Gene Is Statistically Associated With A Higher Risk For Venous Thrombosis," *Thromb. Haemost.* 82(1):1-5 (1999).
Lee, "Von Willebrand Disease, Hemophilia A And B, And Other Factor Deficiencies," *Int. Anesthesiol. Clin.* 42(3):59-76 (2004).
Liu, et al., "Improved coagulation in bleeding disorders by Non-Anticoagulant Sulfated Polysaccharides (NASP)," *Thrombosis and Haemostasis* 95:68-76 (2006).
Luyt, et al., "Low-Molecular-Weight Fucoidan Promotes Therapeutic Revascularization In A Rat Model Of Critical Hindlimb Ischemia," *J. Pharmacol. Exp. Ther.* 305(1):24-30 (2003).

(Continued)

*Primary Examiner*—Shaojia Anna Jiang
*Assistant Examiner*—Scarlett Goon
(74) *Attorney, Agent, or Firm*—Bret E. Field; Bozicevic, Field & Francis LLP

(57) ABSTRACT

Methods for treating bleeding disorders using non-anticoagulant sulfated polysaccharides (NASPs) as procoagulants are disclosed. NASPs can be administered as single agents, or in combination with one another, or with other medications (such as factors VII, VIII and IX) to promote hemostasis. In particular, the use of NASPs in treatment of bleeding disorders, including congenital coagulation disorders, acquired coagulation disorders, and trauma induced hemorrhagic conditions is described.

15 Claims, 8 Drawing Sheets

OTHER PUBLICATIONS

MacGregor, et al., "Metabolism Of Sodium Pentosan Polysulphate In Man Measured By A New Competitive Binding Assay For Sulphated Polysaccharides—Comparison With Effects Upon Anticoagulant Activity, Lipolysis And Platelet Alpha-Granule Proteins," *Thromb. Haemost.* 53(3):411-4 (1985).

Mann, "Thrombin: Can't Live Without It; Probably Die From It," *Chest 124*(3 Suppl):IS-3S (2003).

Mann, "Thrombin Formation," *Chest 124*(3 Suppl):4S-10S (2003).

McAuliffe, et al. *Chem.Indus. Magazine 5*:170-4 (1997).

McCaffrey et al. *Biochem. Biophys. Res. Commun.* 184(2):773-81 (1992).

Millet, et al. "Antithrombotic And Anticoagulant Activities Of A Low Molecular Weight Fucoidan By The Subcutaneous Route," *Thromb. Haemost.* 81:391-5 (1999).

Nordfang, et al. "Inhibition Of Extrinsic Pathway Inhibitor Shortens The Coagulation Time Of Normal Plasma And Of Hemophilia Plasma," *Thromb. Haemost.* 66(4):464-67 (1991).

Novotny, et al. "Purification And Properties Of Heparin-Releasable Lipoprotein-Associated Coagulation Inhibitor," *Blood 78*(2):394-400 (1991).

Orgueria, et al. "Modular Synthesis Of Heparin Oligosaccharides," *Chem. Eur. J.* 9(1):140-69 (2003).

Rapaport, et al., "The Tissue Factor Pathway: How It Has Become A 'Prima Ballerina'," *Thromb. Haemost.* 74(1):7-17 (1995).

Roberts, et al., "Current Concepts Of Hemostasis: Implications For Therapy," *Anesthesiology 100*(3):722-30 (2004).

Sinaÿ, "Sugars Slide Into Heparin Activity," *Nature* 398(6726):377-8 (1999).

Toida et al. *Trends in Glyocscience and Glycotechnology* 15(81):29-46 (2003).

Vicente, et al., "Unbalanced Effects Of 1-23 Dermation Sulfates With Different Sulfation Patterns On Coagulation, Thrombosis And Bleeding," *Thromb Haenos* 86(5):1215-1220 (2001).

Wang, et al., "N-Desulfated Non-Anticoagulant Heparin Inhibits Leukocyte Adhesion And Transmigration In Vitro And Attenuates Acute Peritonitis And Ischemia And Reperfusion Injury In Vivo," *Inflamm. Res.* 51(9):435-43 (2002).

Welsch, et al., "Effect Of Lipoprotein-Associated Coagulation Inhibitor (LACI) On Thromboplastin-Induced Coagulation Of Normal And Hemophiliac Plasmas," *Thromb. Res.* 64(2):213-22 (1991).

Westrick, et al., "Deficiency Of Tissue Factor Pathway Inhibitor Promotes Atherosclerosis And Thrombosis In Mice," *Circulation* 103(25):3044-6 (2001).

Williams, et al., "Comparative Effects Of Heparin And The Sulfatoid GM1474 On Coagulation Parameters In Plasma And Blood From Various Species," *Gen. Pharmacol.* 30(3):337-41 (1998).

Veer Van' T C et al., "Regulation of Tissue Factor Initiated Thrombin Generation by the Stoichiometric Inhibitors Tissue Factor Pathway Inhibitor, Antithrombin-III, and Heparin Cofactor-11", Journal of Biological Chemistry, American Society of Biolochemical Biologists, Birmingham, US, 272(7):4367-4377 (1997).

\* cited by examiner

METHODS FOR TREATING BLEEDING DISORDERS USING SULFATED POLYSACCHARIDES

CROSS-REFERENCE TO RELATED APPLICATIONS

This application is a continuation of U.S. application Ser. No. 11/140,504, filed May 27, 2005, which claims the benefit under 35 U.S.C. §119(e)(1) of U.S. provisional application 60/574,845, filed May 27, 2004, which applications are incorporated herein by reference in their entireties.

TECHNICAL FIELD

This invention relates to the treatment of bleeding disorders, including congenital coagulation disorders, acquired coagulation disorders, and trauma induced hemorrhagic conditions. In particular, this invention relates to the use of non-anticoagulant sulfated polysaccharides (NASP) to improve clotting and hemostasis in hemophilic conditions.

BACKGROUND

Normal blood coagulation is a complex physiological and biochemical process involving activation of a coagulation factor cascade leading to fibrin formation and platelet aggregation along with local vasoconstriction (reviewed by Davie et al., Biochemistry 30:10363, 1991). The clotting cascade is composed of an "extrinsic" pathway thought to be the primary means of normal coagulation initiation and an "intrinsic" pathway contributing to an expanded coagulation response. The normal response to a bleeding insult involves activation of the extrinsic pathway. Activation of the extrinsic pathway initiates when blood comes in contact with tissue factor (TF), a cofactor for factor VII that becomes exposed or expressed on tissues following insult. TF forms a complex with FVII that facilitates the production of FVIIa. FVIIa then associates with TF to convert FX to the serine protease FXa, which is a critical component of the prothrombinase complex. The conversion of prothrombin to thrombin by the FXa/FVa/calcium/phospholipid complex stimulates the formation of fibrin and activation of platelets, all of which is essential to normal blood clotting. Normal hemostasis is further enhanced by intrinsic pathway factors IXa and VIIIa, which also convert FX to FXa.

Blood clotting is inadequate in bleeding disorders, which may be caused by congenital coagulation disorders, acquired coagulation disorders, or hemorrhagic conditions induced by trauma. Bleeding is one of the most serious and significant manifestations of disease, and may occur from a local site or be generalized. Localized bleeding may be associated with lesions and may be further complicated by a defective haemostatic mechanism. Congenital or acquired deficiencies of any of the coagulation factors may be associated with a hemorrhagic tendency. Congenital coagulation disorders include hemophilia, a recessive X-linked disorder involving a deficiency of coagulation factor VIII (hemophilia A) or factor IX (hemophilia B) and von Willebrands disease, a rare bleeding disorder involving a severe deficiency of von Willebrands factor. Acquired coagulation disorders may arise in individuals without a previous history of bleeding as a result of a disease process. For example, acquired coagulation disorders may be caused by inhibitors or autoimmunity against blood coagulation factors, such as factor VIII, von Willebrand factor, factors IX, V, XI, XII and XIII; or by hemostatic disorders such as caused by liver disease, which may be associated with decreased synthesis of coagulation factors. Coagulation factor deficiencies are typically treated by factor replacement which is expensive, inconvenient (intravenous), and not always effective. As many as 20% of patients receiving chronic factor replacement therapy may generate neutralizing antibodies to replacement factors.

Thus, there remains a need for new therapeutic approaches for treating bleeding disorders. A single pharmaceutical agent that is safe, convenient and effective in a broad range of bleeding disorders would favorably impact clinical practice.

SUMMARY OF THE INVENTION

The present invention provides methods and compositions for treating bleeding disorders using non-anticoagulant sulfated polysaccharides (NASPs) as procoagulants. NASPs can be administered as single agents, or in combination with one another, or with other hemostatic agents. In particular, the use of NASPs in treatment of bleeding disorders, including congenital coagulation disorders, acquired coagulation disorders, and trauma induced hemorrhagic conditions is described.

In one aspect, the invention provides a method for treating a subject in need of enhanced blood coagulation comprising administering a therapeutically effective amount of a composition comprising a non-anticoagulant sulfated polysaccharide (NASP) to the subject. In certain embodiments, the invention provides a method for treating a subject having a bleeding disorder comprising administering a therapeutically effective amount of a composition comprising a NASP to the subject. In certain embodiments, the NASP is selected from the group consisting of N-acetyl-heparin (NAH), N-acetyl-de-O-sulfated-heparin (NA-de-o-SH), de-N-sulfated-heparin (De-NSH), de-N-sulfated-acetylated-heparin (De-NSAH), periodate-oxidized heparin (POH), chemically sulfated laminarin (CSL), chemically sulfated alginic acid (CSAA), chemically sulfated pectin (CSP), dextran sulfate (DXS), heparin-derived oligosaccharides (HDO), pentosan polysulfate (PPS), and fucoidan.

In other embodiments the NASP is selected from the group consisting of low molecular weight fragments of the previously listed compounds. In preferred embodiments the fragment of the NASP decreases blood clotting time when tested in the dPT assay. In one embodiment, the NASP is a fragment of fucoidan that decreases blood clotting time when tested in the dPT assay.

In further embodiments, the NASP can be coadministered with one or more different NASPs and/or in combination with one or more other therapeutic agents.

In certain embodiments, a NASP is administered to a subject to treat a bleeding disorder selected from the group consisting of hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

In certain embodiments, a NASP is administered to a subject to treat a congenital coagulation disorder or an acquired coagulation disorder caused by a blood factor deficiency. The blood factor deficiency may be caused by deficiencies of one or more factors, including but not limited to, factor V, factor VII, factor VIII, factor IX, factor XI, factor XII, factor XIII, and von Willebrand factor.

In certain embodiments, the subject having a bleeding disorder is administered a therapeutically effective amount of a composition comprising a NASP in combination with another therapeutic agent. For example, the subject may be administered a therapeutically effective amount of a composition comprising a NASP and one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant such as thrombin; an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa. Therapeutic agents used to treat a subject having a bleeding disorder can be administered in the same or different compositions and concurrently, before, or after administration of a NASP.

In another aspect, the invention provides a method for reversing the effects of an anticoagulant in a subject, the method comprising administering a therapeutically effective amount of a composition comprising a non-anticoagulant sulfated polysaccharide (NASP) to the subject. In certain embodiments, the subject may have been treated with an anticoagulant including, but not limited to, heparin, a coumarin derivative, such as warfarin or dicumarol, tissue factor pathway inhibitor (TFPI), antithrombin III, lupus anticoagulant, nematode anticoagulant peptide (NAPc2), active-site blocked factor VIIa (factor VIIai), factor IXa inhibitors, factor Xa inhibitors, including fondaparinux, idraparinux, DX-9065a, and razaxaban (DPC906), inhibitors of factors Va and VIIIa, including activated protein C (APC) and soluble thrombomodulin, thrombin inhibitors, including hirudin, bivalirudin, argatroban, and ximelagatran. In certain embodiments, the anticoagulant in the subject may be an antibody that binds a clotting factor, including but not limited to, an antibody that binds to Factor V, Factor VII, Factor VIII, Factor IX, Factor X, Factor XIII, Factor II, Factor XI, Factor XII, von Willebrands factor, prekallikrein, or high molecular weight kininogen (HMWK).

In certain embodiments, a NASP can be coadministered with one or more different NASPs and/or in combination with one or more other therapeutic agents for reversing the effects of an anticoagulant in a subject. For example, the subject may be administered a therapeutically effective amount of a composition comprising a NASP and one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant, such as an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa. Therapeutic agents used in combination with a NASP to reverse the effects of an anticoagulant in a subject can be administered in the same or different compositions and concurrently, before, or after administration of the NASP.

In another aspect, the invention provides a method for treating a subject undergoing a surgical or invasive procedure wherein improved blood clotting would be desirable, comprising administering a therapeutically effective amount of a composition comprising a non-anticoagulant sulfated polysaccharide (NASP) to the subject. In certain embodiments, the NASP can be coadministered with one or more different NASPs and/or in combination with one or more other therapeutic agents to the subject undergoing a surgical or invasive procedure. For example, the subject may be administered a therapeutically effective amount of one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant, such as an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa. Therapeutic agents used to treat a subject undergoing a surgical or invasive procedure can be administered in the same or different compositions and concurrently, before, or after administration of the NASP.

In another aspect, the invention provides a method of inhibiting TFPI activity in a subject, the method comprising administering a therapeutically effective amount of a composition comprising a NASP to the subject.

In another aspect, the invention provides a method of inhibiting TFPI activity in a biological sample, the method comprising combining the biological sample (e.g., blood or plasma) with a sufficient amount of a non-anticoagulant sulfated polysaccharide (NASP) to inhibit TFPI activity.

In another aspect, the invention provides a composition comprising a NASP. In certain embodiments, the NASP is selected from the group consisting of N-acetyl-heparin (NAH), N-acetyl-de-O-sulfated-heparin (NA-de-o-SH), de-N-sulfated-heparin (De-NSH), de-N-sulfated-acetylated-heparin (De-NSAH), periodate-oxidized heparin (POH), chemically sulfated laminarin (CSL), chemically sulfated alginic acid (CSAA), chemically sulfated pectin (CSP), dextran sulfate (DXS), heparin-derived oligosaccharides (HDO), pentosan polysulfate (PPS), and fucoidan. In other embodiments the NASP is selected from the group consisting of low molecular weight fragments of the previously listed compounds. In certain embodiments, the composition may further comprise a pharmaceutically acceptable excipient. In certain embodiments, the composition may further comprise one or more different NASPs, and/or one or more therapeutic agents, and/or reagents. For example, the composition may further comprise one or more factors selected from the group consisting of factor XI, factor XII, prekallikrein, high molecular weight kininogen (HMWK), factor V, factor VII, factor VIII, factor IX, factor X, factor XIII, factor II, and von Willebrands factor, tissue factor, factor VIIa, factor Va, and factor Xa, factor IXa, factor XIa, factor XIIa, and VIIIa; and/or one or more reagents selected from the group consisting of APTT reagent, thromboplastin, fibrin, TFPI, Russell's viper venom, micronized silica particles, ellagic acid, sulfatides, and kaolin.

In another aspect, the invention provides a method of measuring acceleration of clotting by a NASP in a biological sample, the method comprising:
  a) combining the biological sample with a composition comprising the NASP,
  b) measuring the clotting time of the biological sample, c) comparing the clotting time of the biological sample to the clotting time of a corresponding biological sample not exposed to the NASP, wherein a decrease in the clotting time of the biological sample exposed to the NASP, if observed, is indicative of a NASP that accelerates clotting.

In certain embodiments, one or more different NASPs and/or therapeutic agents, and/or reagents can be added to the biological sample for measurements of clotting time. For example, one or more factors can be added, including but not limited to, factor XI, factor XII, prekallikrein, high molecular weight kininogen (HMWK), factor V, factor VII, factor VIII, factor IX, factor X, factor XIII, factor II, and von Willebrands factor, tissue factor, factor VIIa, factor Va, and factor Xa, factor IXa, factor XIa, factor XIIa, and VIIIa; and/or one or more reagents, including but not limited to, APTT reagent, tissue factor, thromboplastin, fibrin, TFPI, Russell's viper venom, micronized silica particles, ellagic acid, sulfatides, and kaolin.

These and other embodiments of the subject invention will readily occur to those of skill in the art in view of the disclosure herein.

BRIEF DESCRIPTION OF THE FIGURES

FIG. 2 shows a plot of clotting time (seconds) versus NASP concentration (nM). Data points shown are mean values from duplicate measurements.

FIG. 3 shows a plot of clotting time (seconds) versus NASP concentration (mM). Data points shown are mean values from duplicate measurements.

FIG. 7 shows a plot of clotting time (seconds) versus NASP concentration (nM). Clotting times were determined using the dPT assay. Data points shown are mean values from duplicate measurements.

FIG. 8 shows a plot of clotting time (seconds) versus NASP concentration (nM). Data points shown are mean values from duplicate measurements.

DETAILED DESCRIPTION OF THE INVENTION

Figure 1:
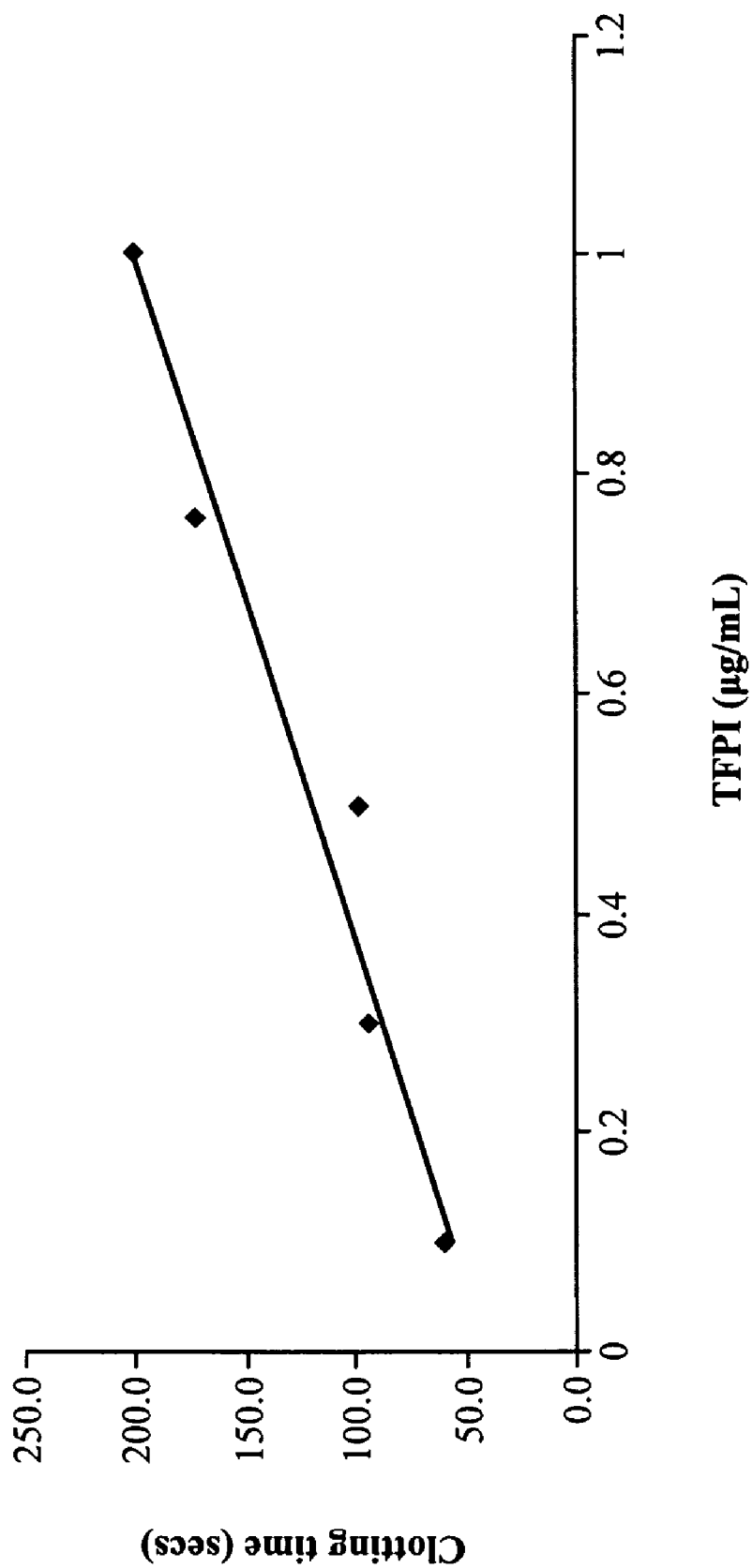
FIG. 1 shows the increase in clotting time of hemophilia A (Hem-A) plasma in the presence of tissue factor pathway inhibitor (TFPI) determined by the dPT assay. A plot of clotting time (seconds) versus TFPI concentration (μg/ml) shows that clotting time increases linearly with TFPI dose.

The practice of the present invention will employ, unless otherwise indicated, conventional methods of pharmacology, chemistry, biochemistry, coagulation, recombinant DNA techniques and immunology, within the skill of the art. Such techniques are explained fully in the literature. See, e.g., *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a NASP" includes a mixture of two or more such agents, and the like.

A "NASP" as used herein refers to a sulfated polysaccharide that exhibits anticoagulant activity in a dilute prothrombin time (dPT) or activated partial thromboplastin time (aPTT) clotting assay that is no more than one-third, and preferably less than one-tenth, the molar anticoagulant (statistically significant increase in clotting time) activity of unfractionated heparin (MW range 8,000 to 30,000; mean 18,000 daltons). NASPs may be purified and/or modified from natural sources (e.g. brown algae, tree bark, animal tissue) or may be synthesized de novo and may range in molecular weight from 100 daltons to 1,000,000 daltons. NASPs may be used in the methods of the invention for improving hemostasis in treating bleeding disorders, particularly those associated with deficiencies of coagulation factors or for reversing the effects of anticoagulants. The ability of NASPs to promote clotting and reduce bleeding is readily determined using various in vitro clotting assays. (e.g., dPT and aPTT assays) and in vivo bleeding models (e.g. tail snip, transverse cut, whole blood clotting time, or cuticle bleeding time determination in hemophilic mice or dogs). See, e.g., PDR Staff. Physicians' Desk Reference. 2004, Anderson et al. (1976) Thromb. Res. 9:575-580; Nordfang et al. (1991) Thromb Haemost. 66:464-467; Welsch et al. (1991) Thrombosis Research 64:213-222; Broze et al. (2001) Thromb Haemost 85:747-748; Scallan et al. (2003) Blood. 102:2031-2037; Pijnappels et al. (1986) Thromb. Haemost. 55:70-73; and Giles et al. (1982) Blood 60:727-730.

A "procoagulant" as used herein refers to any factor or reagent capable of initiating or accelerating clot formation. A procoagulant of the invention includes any activator of the intrinsic or extrinsic coagulation pathways, such as a clotting factor selected from the group consisting of factor Xa, factor IXa, factor XIa, factor XIIa, and VIIIa, prekallekrein, high-molecular weight kininogen, tissue factor, factor VIIa, and factor Va. Other reagents that promote clotting include kallikrein, APTT initiator (i.e., a reagent containing a phospholipid and a contact activator), Russel's viper venom (RVV time), and thromboplastin (for dPT). Contact activators that can be used in the methods of the invention as procoagulant reagents include micronized silica particles, ellagic acid, sulfatides, kaolin or the like known to those of skill in the art. Procoagulants may be from a crude natural extract, a blood or plasma sample, isolated and substantially purified, synthetic, or recombinant. Procoagulants may include naturally occurring clotting factors or fragments, variants or covalently modified derivatives thereof that retain biological activity (i.e., promote clotting). Optimal concentrations of the procoagulant can be determined by those of skill in the art.

The term "polysaccharide," as used herein, refers to a polymer comprising a plurality (i.e., two or more) of covalently linked saccharide residues. Linkages may be natural or unnatural. Natural linkages include, for example, glycosidic bonds, while unnatural linkages may include, for example, ester, amide, or oxime linking moieties. Polysaccharides may have any of a wide range of average molecular weight (MW) values, but generally are of at least about 100 daltons. For example, the polysaccharides can have molecular weights of at least about 500, 1000, 2000, 4000, 6000, 8000, 10,000, 20,000, 30,000, 50,000, 100,000, 500,000 daltons or even higher. Polysaccharides may have straight chain or branched structures. Polysaccharides may include fragments of polysaccharides generated by degradation (e.g., hydrolysis) of larger polysaccharides. Degradation can be achieved by any of a variety of means known to those skilled in the art including treatment of polysaccharides with acid, base, heat, or enzymes to yield degraded polysaccharides. Polysaccharides may be chemically altered and may have modifications, including but not limited to, sulfation, polysulfation, esterification, and methylation.

The term "derived from" is used herein to identify the original source of a molecule but is not meant to limit the method by which the molecule is made which can be, for example, by chemical synthesis or recombinant means.

The terms "variant," "analog" and "mutein" refer to biologically active derivatives of the reference molecule, that retain desired activity, such as clotting activity in the treatment of a bleeding disorder described herein. In general, the terms "variant" and "analog" in reference to a polypeptide (e.g., clotting factor) refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem Biol. (2000) 7:463-473; and Simon et al., Proc. Natl. Acad. Sci. USA (1992) 89:9367-9371 for descriptions of peptoids). Preferably, the analog or mutein has at least the same clotting activity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "derivative" is intended any suitable modification of the reference molecule of interest or of an analog thereof, such as sulfation, acetylation, glycosylation, phosphorylation, polymer conjugation (such as with polyethylene glycol), or other addition of foreign moieties, so long as the desired biological activity (e.g., clotting activity, inhibition of TFPI activity) of the reference molecule is retained. For example, polysaccharides may be derivatized with one or more organic or inorganic groups. Examples include polysaccharides substituted in at least one hydroxyl group with another moiety (e.g., a sulfate, carboxyl, phosphate, amino, nitrile, halo, silyl, amido, acyl, aliphatic, aromatic, or a saccharide group), or where a ring oxygen has been replaced by sulfur, nitrogen, a methylene group, etc. Polysaccharides may be chemically altered, for example, to improve procoagulant function. Such modifications may include, but are not limited to, sulfation, polysulfation, esterification, and methylation. Methods for making analogs and derivatives are generally available in the art.

By "fragment" is intended a molecule consisting of only a part of the intact full-length sequence and structure. A fragment of a polysaccharide may be generated by degradation (e.g., hydrolysis) of a larger polysaccharide. Active fragments of a polysaccharide will generally include at least about 2-20 saccharide units of the full-length polysaccharide, preferably at least about 5-10 saccharide units of the full-length molecule, or any integer between 2 saccharide units and the full-length molecule, provided that the fragment in question retains biological activity, such as clotting activity and/or the ability to inhibit TFPI activity. A fragment of a polypeptide can include a C-terminal deletion an N-terminal deletion, and/or an internal deletion of the native polypeptide. Active fragments of a particular protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the fill-length molecule, or any integer between 5 amino acids and the full-length sequence, provided that the fragment in question retains biological activity, such as clotting activity, as defined herein.

"Substantially purified" generally refers to isolation of a substance (e.g., sulfated polysaccharide) such that the substance comprises the majority percent of the sample in which it resides. Typically in a sample a substantially purified component comprises 50%, preferably 80%-85%, more preferably 90-95% of the sample. Techniques for purifying polysaccharides, polynucleotides, and polypeptides of interest are well-known in the art and include, for example, ion-exchange chromatography, affinity chromatography and sedimentation according to density.

By "isolated" is meant, when referring to a polysaccharide or polypeptide, that the indicated molecule is separate and discrete from the whole organism with which the molecule is found in nature or is present in the substantial absence of other biological macro-molecules of the same type.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN; Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin. Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species.

The term "patient," refers to a living organism suffering from or prone to a condition that can be prevented or treated by administration of a NASP of the invention, and includes both humans and animals.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

By "therapeutically effective dose or amount" of a NASP, blood factor, or other therapeutic agent is intended an amount that, when administered as described herein, brings about a positive therapeutic response, such as reduced bleeding or shorter clotting times.

The term "bleeding disorder" as used herein refers to any disorder associated with excessive bleeding, such as a congenital coagulation disorder, an acquired coagulation disorder, or a trauma induced hemorrhagic condition. Such bleeding disorders include, but are not limited to, hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

II. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

A. General Overview

Blood clotting disorders including hemophilia (Hem) A and Hem B, severe von Willebrand disease (svWD), and severe factor VII (FVII) deficiency have typically been treated by factor replacement, e.g., factor VIII for Hem A and svWD, factor IX for Hem B, and factor VII(a) for FVII-deficiency and others (recently reviewed in Bishop et al. (2004) Nat. Rev. Drug Discov. 3:684-694; Carcao et al. (2004) Blood Rev. 18:101-113; Roberts et al. (2004) Anesthesiology 100:722-730; and Lee (2004) Int. Anesthesiol. Clin. 42:59-76). While such therapies are often effective, characteristics limiting utility include high cost, inconvenience (i.e. intravenous administration), and neutralizing antibody generation (Bishop et al., supra; Carcao et al., supra; Roberts et al., supra; Lee, supra; and Bohn et al. (2004) Haemophilia 10 Suppl. 1:2-8). While FVIIa is increasingly utilized in various bleeding disorders (Roberts et al., supra), alternative single compound procoagulant therapies devoid of aforementioned constraints and with broad application are of interest.

One general approach to improving hemostasis in individuals with bleeding disorders is to improve the initiation of clotting by upregulating the extrinsic pathway of blood coagulation. While the intrinsic and extrinsic pathways of coagulation contribute to thrombin generation and fibrin clot formation (Davie et al. (1991) Biochemistry 30:10363-10370), the extrinsic—or tissue factor (TF) mediated—path is critical for initiation, and contributes to propagation of coagulation in vivo (Mann (2003) Chest 124 (3 Suppl):1S-3S; Rapaport et al. (1995) Thromb. Haemost. 74:7-17). One potential mechanism for upregulating extrinsic pathway activity is the attenuation of Tissue Factor Pathway Inhibitor (TFPI). TFPI is a Kunitz-type proteinase inhibitor of FVIIa/TF that provides tonic downregulation of extrinsic pathway activation (see Broze (1992) Semin. Hematol. 29:159-169; Broze (2003) J. Thromb. Haemost. 1:1671-1675; and Johnson et al. (1998) Coron. Artery Dis. 9(2-3):83-87 for review). Indeed, heterozygous TFPI deficiency in mice can result in exacerbation of thrombus formation (Westrick et al. (2001) Circulation 103:3044-3046), and TFPI gene mutation is a risk factor for thrombosis in humans (Kleesiek et al. (1999) Thromb. Haemost. 82:1-5). Regulating clotting in hemophilia via the targeting of TFPI was described by Nordfang et al. and Wun et al., who showed that anti-TFPI antibodies could shorten the coagulation time of hemophilic plasma (Nordfang et al. (1991) Thromb. Haemost. 66:464-467; Welsch et al. (1991) Thromb. Res. 64:213-222) and that anti-TFPI IgG improved the bleeding time of rabbits that were factor VIII-deficient (Erhardtsen et al. (1995) Blood Coagul. Fibrinolysis 6:388-394).

As a class, sulfated polysaccharides are characterized by a plethora of biological activities with often favorable tolerability profiles in animals and humans. These polyanionic molecules are often derived from plant and animal tissues and encompass a broad range of subclasses including heparins, glycosaminoglycans, fucoidans, carrageenans, pentosan polysulfates, and dermatan or dextran sulfates (Toida et al. (2003) Trends in Glycoscience and Glycotechnology 15:29-46). Lower molecular weight, less heterogeneous, and chemically synthesized sulfated polysaccharides have been reported and have reached various stages of drug development (Sinay (1999) Nature 398:377-378; Bates et al. (1998) Coron. Artery Dis. 9:65-74; Orgueira et al. (2003) Chemistry 9:140-169; McAuliffe (1997) Chemical Industry Magazine 3:170-174; Williams et al. (1998) Gen. Pharmacol. 30:337-341). Heparin-like sulfated polysaccharides exhibit differential anticoagulant activity mediated through antithrombin III and/or heparin cofactor II interactions (Toida et al., supra). Notably, certain compounds, of natural origin or chemically modified, exhibit other biological activities at concentrations (or doses) at which anticoagulant activity is not substantial (Williams et al. 1998) Gen. Pharmacol. 30:337-341; Wan et al. (2002) Inflamm. Res. 51:435-443; Bourin et al. (1993) Biochem. J. 289 (Pt 2):313-330; McCaffrey et al. (1992) Biochem. Biophys. Res. Commun. 184:773-781; Luyt et al. (2003) J. Pharmacol. Exp. Ther. 305:24-30). In addition, heparin sulfate has been shown to exhibit strong interactions with TFPI (Broze (1992) Semin. Hematol. 29:159-169; Broze (2003) J. Thromb. Haemost. 1:1671-1675; Johnson et al. (1998) Coron. Artery Dis. 9:83-87; Novotny et al. (1991) Blood; 78(2):394-400).

As described herein, certain sulfated polysaccharides interact with TFPI and inhibit its activity at lower concentrations than those associated with anticoagulation. Such molecules may be of use in settings where clot formation is compromised.

B. NASPs as Promoters of Clotting

The present invention is based on the discovery that non-anticoagulant sulfated polysaccharides (NASPs) can be used as procoagulants in treatment of patients with bleeding disorders. A novel approach for regulating hemostasis has been discovered by the inventors herein that, paradoxically, utilizes sulfated polysaccharides, such as heparin-like sulfated polysaccharides to promote clotting. Selected sulfated polysaccharides described herein are largely devoid of anticoagulant activity, or exhibit clot-promoting activity at concentrations significantly lower than the concentration at which they exhibit anticoagulant activity, and are hence denoted "non-anticoagulant sulfated polysaccharides."

As shown in Examples 4-6, NASPs promote clotting of plasma from subjects that have hemophilia A (Hem-A) or hemophilia B (Hem-B) according to dilute prothrombin time (dPT) and activated partial thromboplastin time (aPTT) clotting assays. In addition, NASPs reduce bleeding time in hemophilia A and B mouse models following injury (Example 7). In the experiments disclosed herein, certain candidate NASPs are shown in clotting assays to demonstrate at least ten-fold lower anticoagulant activity as compared to heparin. Moreover, a subset of NASPs, including pentosan polysulfate (PPS) and fucoidan, inhibited Tissue Factor Pathway Inhibitor (TFPI) and improved (i.e. accelerated) the clotting time of human hemophilia A and hemophilia B plasmas or plasma with reduced FVII levels when tested at concentrations ranging from 4-500 nM in dilute prothrombin time (dPT) assays. Improved hemostasis in vivo was observed in mice with hemophilia A or B following low dose subcutaneous administration of PPS or fucoidan, or a combination of NASP and a factor supplement. Increased survival of factor deficient mice following a bleeding challenge was also observed. These results indicate that systemic administration of select NASPs may represent a unique approach for regulating hemostasis in bleeding disorders.

Thus, the invention relates to the use of NASPs to control hemostasis in subjects with bleeding disorders, including congenital coagulation disorders, acquired coagulation disorders, and trauma induced hemorrhagic conditions.

C. NASPs

NASPs for use in the methods of the invention are sulfated polysaccharides that have procoagulant activity. The noncoagulant properties of potential NASPs are determined using dilute prothrombin time (dPT) or activated partial thromboplastin time (aPTT) clotting assays. Noncoagulant sulfated polysaccharides exhibit no more than one-third, and preferably less than one-tenth, the anticoagulant activity (measured by statistically significant increase in clotting time) of unfractionated heparin (MW range 8,000 to 30,000; mean 18,000 daltons).

Sulfated polysaccharides with potential NASP activity include, but are not limited to, glycosaminoglycans (GAGs), heparin-like molecules including N-acetyl heparin (Sigma-Aldrich, St. Louis, Mo.) and N-desulfated heparin (Sigma-Aldrich), sulfatoids, polysulfated oligosaccharides (Karst et al. (2003) Curr. Med. Chem. 10:1993-2031; Kuszmann et al. (2004) Pharmazie. 59:344-348), chondroitin sulfates (Sigma-Aldrich), dermatan sulfate (Celsus Laboratories Cincinnati, Ohio), fucoidan (Sigma-Aldrich), pentosan polysulfate (PPS) (Ortho-McNeil Pharmaceuticals, Raritan, N.J.), fucopyranon sulfates (Katzman et al. (1973) J. Biol. Chem. 248:50-55), and novel sulfatoids such as GM1474 (Williams et al. (1998) General Pharmacology 30:337) and SR 80258A (Burg et al. (1997) Laboratory Investigation 76:505), and novel heparinoids, and their analogs. NASPs may be purified and/or modified from natural sources (e.g. brown algae, tree bark, animal tissue) or may be synthesized de novo and may range in molecular weight from 100 daltons to 1,000,000 daltons. Additional compounds with potential NASP activity include periodate-oxidized heparin (POH) (Neoparin, Inc., San Leandro, Calif.), chemically sulfated laminarin (CSL) (Sigma-Aldrich), chemically sulfated alginic acid (CSAA) (Sigma-Aldrich), chemically sulfated pectin (CSP) (Sigma-Aldrich), dextran sulfate (DXS) (Sigma-Aldrich), heparin-derived oligosaccharides (HDO) (Neoparin, Inc., San Leandro, Calif.).

In principle, any free hydroxyl group on a monosaccharide component of a glycoconjugate can be modified by sulfation to produce a sulfated glycoconjugate for potential use as a NASP in the practice of the invention. For example, such sulfated glycoconjugates may include without limitation sulfated mucopolysaccharides (D-glucosamine and D-glucoronic acid residues), curdlan (carboxymethyl ether, hydrogen sulfate, carboxymethylated curdlan) (Sigma-Aldrich), sulfated schizophyllan (Itoh et al. (1990) Int. J. Immunopharmacol. 12:225-223; Hirata et al. (1994) Pharm. Bull. 17:739-741), sulfated glycosaminoglycans, sulfated polysaccharide-peptidoglycan complex, sulfated alkyl malto-oligosaccharide (Katsuraya et al. (1994) Carbohydr Res. 260:51-61), amylopectin sulfate, N-acetyl-heparin (NAH) (Sigma-Aldrich), N-acetyl-de-O-sulfated-heparin (NA-de-b-SH) (Sigma-Aldrich), de-N-sulfated-heparin (De-NSH) (Sigma-Aldrich), and De-N-sulfated-acetylated-heparin (De-NSAH) (Sigma-Aldrich).

The ability of NASPs to promote clotting and reduce bleeding is readily determined using various in vitro clotting assays (e.g., dPT and aPTT assays) and in vivo bleeding models (e.g. tail snip or cuticle bleeding time determination in hemophilic mice or dogs). See, e.g., PDR Staff. Physicians' Desk Reference. 2004, Anderson et al. (1976) Thromb. Res. 9:575-580; Nordfang et al. (1991) Thromb Haemost. 66:464-467; Welsch et al. (1991) Thrombosis Research 64:213-222; Broze et al. (2001) Thromb Haemost 85:747-748; Scallan et al. (2003) Blood. 102:2031-2037; Pijnappels et al. (1986) Thromb. Haemost. 55:70-73; and Giles et al. (1982) Blood 60:727-730. Clotting assays may be performed in the presence of NASPs and one or more blood factors, procoagulants, or other reagents. For example, one or more factors can be added, including but not limited to, factor XI, factor XII, prekallikrein, high molecular weight kininogen (HMWK), factor V, factor VII, factor VIII, factor IX, factor X, factor XIII, factor II, and von Willebrands factor, tissue factor, factor VIIa, factor Va, and factor Xa, factor IXa, factor XIa, factor XIIa, and VIIIa; and/or one or more reagents, including but not limited to, APTT reagent, thromboplastin, fibrin, TFPI, Russell's viper venom, micronized silica particles, ellagic acid, sulfatides, and kaolin.

Figure 2:
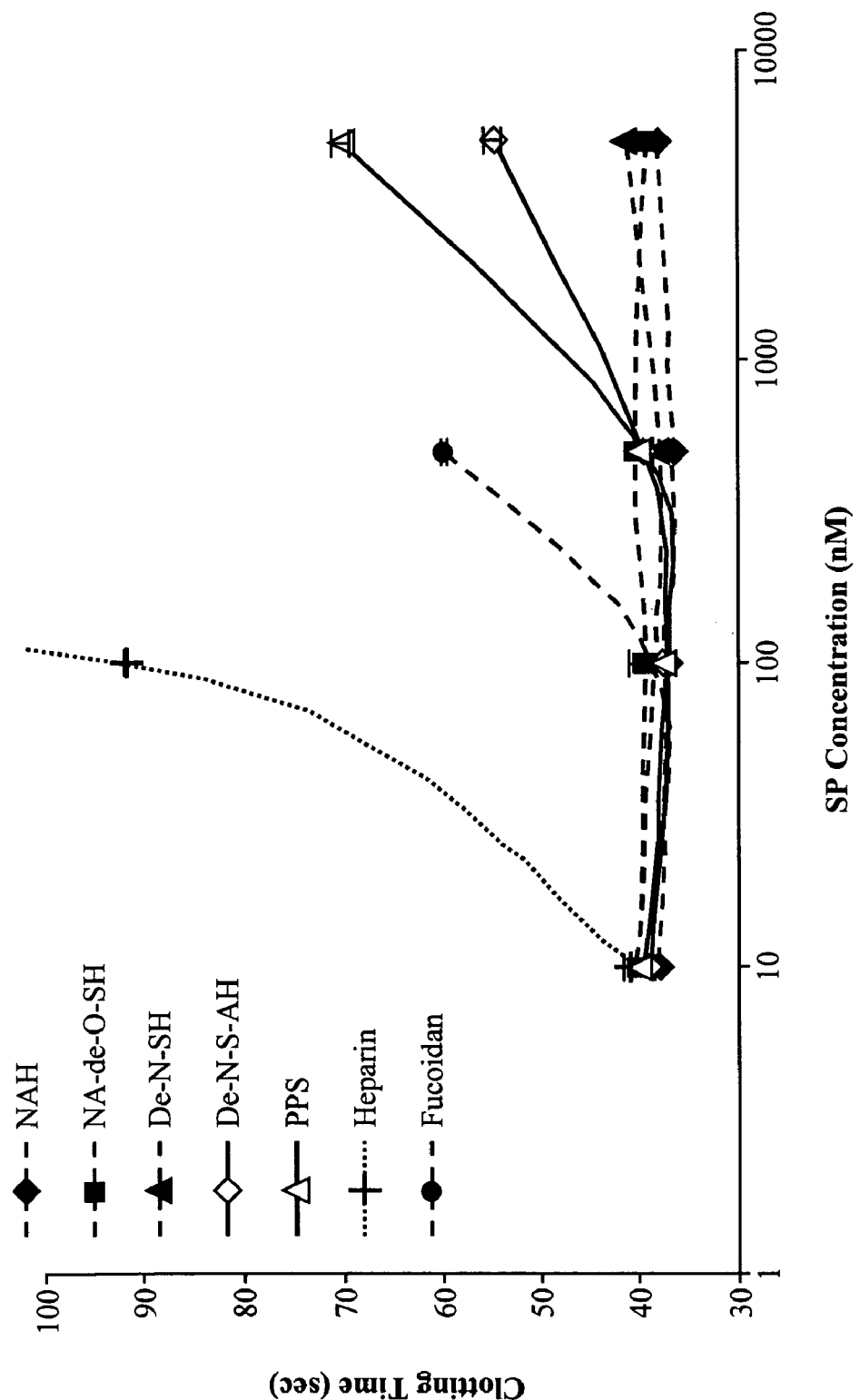
FIG. 2 compares anticoagulant activities of potential NASPs, N-acetyl-heparin (NAH), N-acetyl-de-O-sulfated-heparin (NA-de-O—SH), de-N-sulfated-heparin (De-N—SH), de-N-sulfated-acetylated-heparin (De-N—SAH), pentosan polysulfate (PPS), fucoidan, and heparin. Selected polysaccharides were tested at various concentrations in Hem-A plasma.
Figure 3:
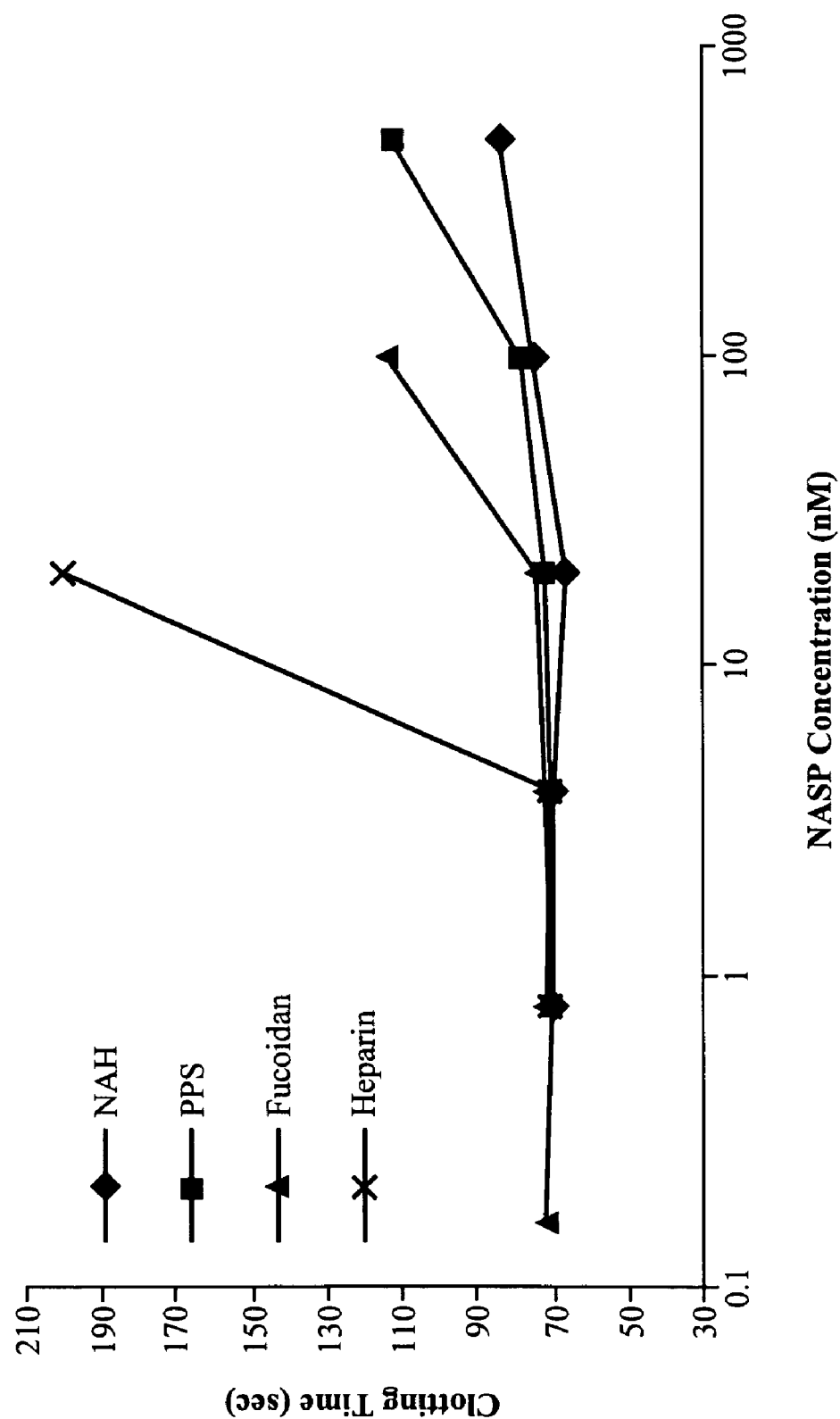
FIG. 3 compares the effects of NAH, PPS, fucoidan, and heparin on clotting time of Hem-A plasma containing 1.25% FACT plasma, as determined using the aPTT assay.

Examples 3-4 and FIGS. 2-3 confirm that the agents referred to herein as NASPs are truly "non-anticoagulant," i.e. that they do not significantly increase clotting times over the range of concentrations studied. Such compounds can be used in the methods and compositions of the present invention provided that any anticoagulant activity that they may exhibit only appears at concentrations significantly above the concentration at which they exhibit procoagulant activity. The ratio of the concentration at which undesired anticoagulant properties occur to the concentration at which desired procoagulant activities occur is referred to as the therapeutic index for the NASP in question. The therapeutic index for NASPs of the present invention may be 5, 10, 30, 100, 300, 1000 or more.

D. Pharmaceutical Compositions

Optionally, the NASP compositions of the invention may further comprise one or more pharmaceutically acceptable excipients to provide a pharmaceutical composition. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the NASP or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the NASP (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the NASP compositions described herein are in unit dosage form, meaning an amount of a conjugate or composition of the invention appropriate for a single dose, in a premeasured or pre-packaged form.

The NASP compositions herein may optionally include one or more additional agents, such as hemostatic agents, blood factors, or other medications used to treat a subject for a condition or disease. Particularly preferred are compounded preparations including one or more blood factors such as factor XI, factor XII, prekallikrein, high molecular weight kininogen (HMWK), factor V, factor VII, factor VIII, factor IX, factor X, factor XIII, factor II, factor VIIa, and von Willebrands factor. NASP compositions may also include other procoagulants, such as an activator of the intrinsic coagulation pathway, including but not limited to, factor Xa, factor IXa, factor XIa, factor XIIa, and VIIIa, prekallekrein, and high-molecular weight kininogen; or and activator of the extrinsic coagulation pathway, including but not limited to, tissue factor, factor VIIa, factor Va, and factor Xa. NASP compositions may include naturally occurring, synthetic, or recombinant clotting factors or fragments, variants or covalently modified derivatives thereof that retain biological activity (i.e., promote clotting). Alternatively, such agents can be contained in a separate composition from the NASP and co-administered concurrently, before, or after the NASP composition of the invention.

E. Administration

At least one therapeutically effective cycle of treatment with a NASP will be administered to a subject. By "therapeutically effective cycle of treatment" is intended a cycle of treatment that when administered, brings about a positive therapeutic response with respect to treatment of an individual for a bleeding disorder. Of particular interest is a cycle of treatment with a NASP that improves hemostasis. By "positive therapeutic response" is intended that the individual undergoing treatment according to the invention exhibits an improvement in one or more symptoms of a bleeding disorder, including such improvements as shortened blood clotting times and reduced bleeding and/or reduced need for factor replacement therapy.

In certain embodiments, multiple therapeutically effective doses of compositions comprising one or more NASPs and/or other therapeutic agents, such as hemostatic agents, blood factors, or other medications will be administered. The compositions of the present invention are typically, although not necessarily, administered orally, via injection (subcutaneously, intravenously or intramuscularly), by infusion, or locally. The pharmaceutical preparation can be in the form of a liquid solution or suspension immediately prior to administration, but may also take another form such as a syrup, cream, ointment, tablet, capsule, powder, gel, matrix, suppository, or the like. Additional modes of administration are also contemplated, such as pulmonary, rectal, transdermal, transmucosal, intrathecal, pericardial, intra-arterial, intracerebral, intraocular, intraperitoneal, and so forth. The pharmaceutical compositions comprising NASPs and other agents may be administered using the same or different routes of administration in accordance with any medically acceptable method known in the art.

In a particular embodiment, a composition of the invention is used for localized delivery of a NASP, for example, for the treatment of bleeding as a result of a lesion, injury, or surgery. The preparations according to the invention are also suitable for local treatment. For example, a NASP may be administered by injection at the site of bleeding or in the form of a solid, liquid, or ointment, preferably via an adhesive tape or a wound cover. Suppositories, capsules, in particular gastric-juice-resistant capsules, drops or sprays may also be used. The particular preparation and appropriate method of administration are chosen to target the site of bleeding.

In another embodiment, the pharmaceutical compositions comprising NASPs and/or other agents are administered prophylactically, e.g. before planned surgery. Such prophylactic uses will be of particular value for subjects with known pre-existing blood coagulation disorders.

In another embodiment of the invention, the pharmaceutical compositions comprising NASPs and/or other agents, are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The invention also provides a method for administering a conjugate comprising a NASP as provided herein to a patient suffering from a condition that is responsive to treatment with a NASP contained in the conjugate or composition. The method comprises administering, via any of the herein described modes, a therapeutically effective amount of the conjugate or drug delivery system, preferably provided as part of a pharmaceutical composition. The method of administering may be used to treat any condition that is responsive to treatment with a NASP. More specifically, the compositions herein are effective in treating bleeding disorders, including hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an $alpha_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

Those of ordinary skill in the art will appreciate which conditions a specific NASP can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

Generally, a therapeutically effective amount will range from about 0.01 mg/kg to 200 mg/kg of a NASP daily, more preferably from about 0.01 mg/kg to 20 mg/kg daily, even more preferably from about 0.02 mg/kg to 2 mg/kg daily. Preferably, such doses are in the range of 0.01-50 mg/kg four times a day (QID), 0.01-10 mg/kg QID, 0.01-2 mg/kg QID, 0.01-0.2 mg/kg QID, 0.01-50 mg/kg three times a day (TID), 0.01-10 mg/kg TID, 0.01-2 mg/kg TID, 0.01-0.2 mg/kg TID, 0.01-100 mg/kg twice daily (BID), 0.01-10 mg/kg BID, 0.01-2 mg/kg BID, or 0.01-0.2 mg/kg BID. The amount of compound administered will depend on the potency of the specific NASP and the magnitude or procoagulant effect desired and the route of administration.

A NASP (again, preferably provided as part of a pharmaceutical preparation) can be administered alone or in combination with other NASPs or therapeutic agents, such as hemostatic agents, blood factors, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

A NASP can be administered prior to, concurrent with, or subsequent to other agents. If provided at the same time as other agents, the NASP can be provided in the same or in a different composition. Thus, NASPs and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising a NASP and a dose of a pharmaceutical composition comprising at least one other agent, such as a hemostatic agent or coagulation factor (e.g. FVIII or FIX), which in combination comprise a therapeutically effective dose, according to a particular dosing regimen. Similarly, one or more NASPs and therapeutic agents can be administered in at least one therapeutic dose. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

F. Applications

In one aspect, NASPs may be used in the methods of the invention for improving hemostasis in treating bleeding disorders, particularly those associated with deficiencies of coagulation factors or for reversing the effects of anticoagulants in a subject. NASPs may be administered to a subject to treat bleeding disorders, including congenital coagulation disorders, acquired coagulation disorders, and hemorrhagic conditions induced by trauma. Examples of bleeding disorders that may be treated with NASPs include, but are not limited to, hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy. In certain embodiments, NASPs are used to treat congenital coagulation disorders including hemophilia A, hemophilia B, and von Willebrands disease. In other embodiments, NASPs are used to treat acquired coagulation disorders, including deficiencies of factor VIII, von Willebrand factor, factor IX, factor V, factor XI, factor XII and factor XIII, particularly disorders caused by inhibitors or autoimmunity against blood coagulation factors, or haemostatic disorders caused by a disease or condition that results in reduced synthesis of coagulation factors.

The needs of the patient will depend on the particular bleeding disorder being treated. For example, a NASP may be administered to treat a chronic condition (e.g., a congenital or acquired coagulation factor deficiency) in multiple doses over an extended period. Alternatively, a NASP may be administered to treat an acute condition (e.g., bleeding caused by surgery or trauma, or factor inhibitor/autoimmune episodes in subjects receiving coagulation replacement therapy) in single or multiple doses for a relatively short period, for example one to two weeks. In addition, NASP therapy may be used in combination with other hemostatic agents, blood factors, and medications. For example, the subject may be administered a therapeutically effective amount of one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant, such as an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa. In addition, transfusion of blood products may be necessary to replace blood loss in subjects experiencing excessive bleeding, and in cases of injury, surgical repair may be appropriate to stop bleeding.

The invention also provides a method for reversing the effects of an anticoagulant in a subject, the method comprising administering a therapeutically effective amount of a composition comprising a NASP to the subject. In certain embodiments, the subject may have been treated with an anticoagulant including, but not limited to, heparin, a coumarin derivative, such as warfarin or dicumarol, TFPI, AT III, lupus anticoagulant, nematode anticoagulant peptide (NAPc2), active-site blocked factor VIIa (factor VIIai), factor IXa inhibitors, factor Xa inhibitors, including fondaparinux, idraparinux, DX-9065a, and razaxaban (DPC906), inhibitors of factors Va and VIIIa, including activated protein C (APC) and soluble thrombomodulin, thrombin inhibitors, including hirudin, bivalirudin, argatroban, and ximelagatran. In certain embodiments, the anticoagulant in the subject may be an antibody that binds a clotting factor, including but not limited to, an antibody that binds to Factor V, Factor VII, Factor VIII, Factor IX, Factor X, Factor XIII, Factor II, Factor XI, Factor XII, von Willebrands factor, prekallikrein, or high molecular weight kininogen (HMWK).

In certain embodiments, a NASP can be administered alone or coadministered with one or more different NASPs and/or in combination with one or more other therapeutic agents for reversing the effects of an anticoagulant in the subject. For example, the subject may be administered a therapeutically effective amount of a composition comprising a NASP and one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant, such as an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa.

In another aspect, the invention provides a method for improving clotting in a subject undergoing a surgical or invasive procedure, the method comprising administering a therapeutically effective amount of a composition comprising a non-anticoagulant sulfated polysaccharide (NASP) to the subject. In certain embodiments, the NASP can be administered alone or coadministered with one or more different NASPs and/or in combination with one or more other therapeutic agents to the subject undergoing a surgical or invasive procedure. For example, the subject may be administered a therapeutically effective amount of one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant, such as an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa.

In another aspect, the invention provides a method of inhibiting TFPI activity comprising combining a composition comprising TFPI with a sufficient amount of a NASP to inhibit TFPI activity. In certain embodiments, TFPI activity is inhibited in a subject by a method comprising administering a therapeutically effective amount of a composition comprising a NASP to the subject. In certain embodiments, the invention provides a method of inhibiting TFPI activity in a biological sample, the method comprising combining the biological sample (e.g., blood or plasma) with a sufficient amount of a NASP to inhibit TFPI activity.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Material and Methods

A. Reagents

Heparin and modified heparins, and fucoidan were purchased from Sigma (St. Louis, Mo.). The source of pentosan polysulfate sodium (PPS) was the prescription drug Elmiron obtained from Ortho-McNeil Pharmaceuticals (Raritan, N.J.). Human plasmas were obtained from George King Biomedical (Overland Park, Kans.). Factors VIIa and human recombinant TFPI were from American Diagnostica (Stamford, Conn.) and Factor VIII was prescription ReFacto® obtained from Wyeth Pharmaceuticals (Madison, N.J.). SIMPLASTIN EXCEL and APTT reagent were obtained from bioMerieux (Durham, N.C.) or Organon Teknika (Roseland, N.J.).

B. Animals.

Hem-A mice (homozygous for the exon 16 FVIII KO allele) were licensed from John Hopkins University, and Hem-B mice (homozygous for the exon 1-3 FIX KO) were licensed from University of North Carolina at Chapel Hill. All animal procedures were performed according to "Guide for the Care and Use of Laboratory Animals" (National Research Council. Guide for the care and use of laboratory animals. Washington, D.C.: National Academy Press; 1996) and all procedures were reviewed and approved by an institutional animal care and use committee.

C. Clotting Assays

Activated Partial Thromboplastin Time (aPTT) Assay

The aPTT assay was performed as described previously with modifications (PDR Staff. Physicians' Desk Reference. 2004, Anderson Lo, Barrowcliffe, T. W., Holmer, E., Johnson, E. A., Sims, G. E. C. Thromb. Res. 1976; 9:575-580). 25 mM $CaCl_2$ and fibrin cups (Fisher) were pre-warmed to 37° C. 0.1 ml of thawed human plasma (normal or hemophilic) was added to warmed test tubes. 5 µl of saline (e.g. Sigma) or 5 µl of test agent (e.g., NASP) dissolved in saline was incubated with 95 µl of plasma for 30 minutes at room temperature. APTT reagent (e.g. Organon Teknika) was reconstituted in 3 ml distilled water and 0.1 ml of the reconstituted solution containing the APTT reagent was added to each test tube. 0.2 ml of plasma containing the test agent or saline control and aPTT reagent were transferred from test tubes to pre-warmed fibrin cups and incubated for 2-3 minutes. 0.1 ml of prewarmed 25 mM $CaCl_2$ was added to initiate clotting, and the time for plasma clotting was measured with a BBL FIBROSYSTEM fibrometer.

Dilute Prothrombin Time (dPT) Assay

The dPT assay used was a modified standard clinical PT assay (Nordfang et al. (1991) Thromb Haemost 66:464-467; Welsch et al. (1991) Thrombosis Research 64: 213-222). SIMPLASTIN EXCEL thromboplastin reagent (Organon Teknika) was reconstituted with the manufacturer's diluent and further diluted 1:100 in 0.9% saline. The thromboplastin reagent, 25 mM $CaCl_2$, and plasma samples were prewarmed to 37° C. before initiating the assay. 100 µl of thawed plasma was aliquoted into microcentrifuge tubes. For measurements of inhibition of TFPI activity, 5 µl of saline (e.g. Sigma) or 5 µl of test agent (e.g. sulfated polysaccharide) was added to 95 µl of plasma and incubated for approximately 30 minutes at room temperature. 100 µl of the diluted thromboplastin reagent and 100 µl of 25 mM $CaCl_2$ were added to fibrin cups (Fisher) prewarmed to 37° C. 100 µl of plasma (normal or hemophilic) containing the test agent or saline control was added to the fibrin cups containing the thromboplastin reagent and $CaCl_2$ to initiate clotting. The time for plasma clotting was measured with a BBL FIBROSYSTEM fibrometer.

Animal Bleeding Time Assays

The bleeding time assay can be used to measure changes in hemostasis function in normal or hemophilic (FVIII or FIX or vWF deficient) rodents following administration of a test agent (e.g., vehicle control or NASP). A test agent (e.g., vehicle control or NASP) is administered to a rodent once or twice daily orally, parenterally, or by continuous infusion. For example, 0.1 ml/10 g body weight (subscapular) of a test agent at a dose ranging from 0.1 to 10 mg/kg can be administered with small gauge needles twice a day for at least one day and preferably more than 3 days. On the day bleeding time is assayed, rodents are anesthetized with ketamine/xylazine (or isoflurane). Rodents are lined up on a sterile pad with a petri dish of saline for tail immersion. EMLA creme is applied to the tail of rodents at an intended cut site. For mice, the very tip of the tail is snipped, and the tail is placed into the saline dish and a counter is started. For rats, an 8 mm long by 1 mm deep incision is made on the dorsal part of the rat tail, which is then transferred into saline. The time for cessation of visible bleeding into the saline is recorded. For rodents, bleeding times are approximately 10 minutes for normal control mice and 6 minutes for normal control rats. After completion of the bleeding time assay, the rodent's tail is dried with sterile gauze, verified for hemostasis, and the rodent is returned to the cage. Silver nitrate can be applied to the cut site if necessary.

Alternatively, bleeding times can be measured in mice (Broze et al. (2001) Thromb. Haemost. 85:747-748) or in dogs (Scallan et al. (2003) Blood 102:2031-2037; Pijnappels et al. (1986) Thromb. Haemost. 55:70-73) by other methods. Alternative or additional pharmacodynamic endpoints may include sampling of blood from NASP-treated subjects for direct analysis or for plasma isolation, and measurement of ex vivo clotting times (e.g., Whole Blood Clotting Time and/or PT and/or APTT) or coagulation factor levels.

Whole Blood Clotting Time (WBCT) Assay

The WBCT assay was performed as follows. Mice were briefly anesthetized in an isoflurane chamber. The mice were then bled (e.g. 150 µl) from the retro orbital plexus into plastic blood collection tubes. The tubes were placed in a 37° C. water bath and a stop watch was used to measure clotting time. During this period, the tubes were inverted at 1 minute intervals. The time required for blood clotting (full/not partial clot) was measured.

Statistical Analyses

For the clotting assays, the Student's t-test was used to analyze the significance between NASP-treated samples and vehicle controls. Data from mouse bleeding tests were studied for significance from vehicle controls (or other groups as indicated in the tables below) by one-way Chi-squared analysis. Nearly identical results were obtained by Fisher's exact test.

EXAMPLE 2

TFPI Increases Clotting Time in dPT Assay

The following experiments were performed to demonstrate that TFPI increases clotting time in the dPT assay and to determine a TFPI concentration for use in subsequent NASP experiments. A 100 µg/mL TFPI stock solution (American Diagnostica, Stamford, Conn.) was sequentially diluted in saline to generate TFPI solutions at the following concentrations: 20, 15, 10, 6, and 2 µg/mL. 5 µl of these TFPI dilutions were mixed with 95 µl of FVIII deficient plasma and incubated at room temperature for 30 minutes. dPT assays were performed as follows: SIMPLASTIN thromboplastin was diluted 1:100 in saline and prewarmed to 37° C. 25 mM $CaCl_2$ and 100 µl of test plasma containing TFPI was prewarmed to 37° C. 100 µl SIMPLASTIN thromboplastin and 100 µl of $CaCl_2$ were mixed and clotting time was measured using a BBL fibrometer. The results are summarized in Table 1.

TABLE 1

Clotting Times in Presence of TFPI

| TFPI concentration in plasma (µg/mL) | Clotting time (seconds) |
|---|---|
| 1 | >200 |
| 0.75 | 173 |
| 0.5 | 98 |
| 0.3 | 94 |
| 0.1 | 60 |

TFPI increased the clotting time of Hem-A plasma with a linear dose response (see FIG. 1). Based on these data, a concentration of 0.5 µg/ml TFPI was chosen for assays of NASP procoagulant function.

EXAMPLE 3

Screening for NASPs

Sulfated polysaccharide compounds, including modified heparins, pentosan polysulfate, and fucoidan were tested for anti-coagulant activity and compared to heparin to determine whether they qualified as "non-anticoagulants." The compounds tested are listed in Table 2.

TABLE 2

NASPs Tested for Anti-Coagulant Activity

| NASP | Company/Cat. # | MW (kd) |
|---|---|---|
| N-Acetyl-Heparin (NAH) | Sigma Chem. Co. A8036 | 18 |
| N-Acetyl-de-O-Sulfated-Heparin (NA-de-o-SH) | Sigma Chem. Co. A6039 | 18 |
| De-N-Sulfated-Heparin (De-NSH) | Sigma Chem. Co. D4776 | 18 |
| De-N-Sulfated-Acetylated-Heparin (De-NSAH) | Sigma Chem. Co. D9808 | 18 |
| Pentosan Polysulphate Sodium (PPS) | Ivax Pharmaceuticals, Inc. NDC 17314-9300-1 | 5 |
| Fucoidan | Sigma Chem. Co. F5631 | 100 |
| Sodium Heparin | Sigma Chem. Co. H4784 | 18 |

Test compounds were diluted to 100 µM, 10 µM, 2 µM and 200 nM. For each test compound, 12.5 µl of a diluted solution containing the test compound was added to 237.5 µl of Hem-A plasma and incubated at room temperature. 100 µl of plasma containing the test compound was removed for dPT assays of plasma clotting time as described in Example 2. The results are summarized in Table 3 below.

TABLE 3

Effect of NASPs on Clotting Time* According to dPT Assay

| NASP Concentration (nM) | NAH | NA-de-O-SH | De-N-SH | De-N-S-AH | PPS | Heparin | Fucoidan |
|---|---|---|---|---|---|---|---|
| 10 | 38 | 40 | 40 | 39 | 39 | 40 | 39 |
| 100 | 37 | 40 | 38 | 37 | 37 | 92 | 38 |
| 500 | 36 | 40 | 38 | 40 | 40 | 400 | 60 |
| 5000 | 38 | 40 | 41 | 55 | 70 | | |

*The values shown are clotting times (seconds) for selected polysaccharides. The clotting time of Hem-A plasma in the absence of NASPs is 41.5 seconds.

As shown in Table 3 and FIG. 2, heparin at concentrations exceeding 10 nM was markedly anticoagulant whereas N-acetyl heparin (NAH), N-acetyl-de-O-sulfated heparin (NA-de-O—SH), de-N-sulfated heparin (De-N—SH) showed little or no prolongation of clotting time at concentrations >5000 nM. Likewise, fucoidan and PPS were only weakly anticoagulant, exhibiting 50% prolongation of clotting time at concentrations approximately 10- to 100-fold higher, respectively, than heparin and are hence denoted "non-anticoagulant." A nearly identical profile was observed with normal human plasma (data not shown).

EXAMPLE 4

Effect of NASPs on Clotting of Human Plasma According to aPTT Assay

The effect of NASPs on the clotting time of plasma was also measured using an aPTT assay to determine whether they qualify as "non-anticoagulants." Dilutions of FACT, a "normal" human reference plasma (George King Biomedical), were made in human Hem-A plasma to generate plasma with concentrations of normal plasma from 0.31-100%. The aPTT assay was then performed as follows: 100 µl of a FACT-Hem-A plasma mixture and 100 µl of aPTT reagent were mixed and incubated at 37° C. for 3 minutes. 100 µl of $CaCl_2$ was added, and the time for plasma clotting was measured using a BBL fibrometer. The results are shown in Table 4.

TABLE 4

Effect of FACT Concentration on Clotting Time

| FACT conc. in Hem-A plasma (%) | aPTT time (seconds) |
|---|---|
| 100 | 40 |
| 50 | 40 |
| 25 | 42 |
| 10 | 50 |
| 5 | 54 |
| 2.5 | 60 |
| 1.25 | 64 |
| 0.63 | 69 |
| 0.31 | 76 |
| 0 | 96 |

Based on this data, a FACT concentration of 1.25% was chosen for assays screening NASPs for procoagulant activity. The effect of NASPs on the clotting time of plasma was determined as follows: 5 µl of a NASP was added to 95 µl of 1.25% FACT diluted in human Hem-A plasma and incubated at room temperature for 30 minutes. aPTT assays were performed to determine plasma clotting time as described in Example 1. The results are shown in Table 5.

TABLE 5

Effect of NASPs on Plasma Clotting Time According to the aPTT Assay

| NASP Concentration (nM) | NAH clotting time (sec) | PPS clotting time (sec) | Fucoidan clotting time (sec) | Heparin clotting time (sec) |
|---|---|---|---|---|
| 0.16 | | | 71 | |
| 0.8 | 70 | 70 | 70 | 70 |
| 4 | 69 | 71 | 71 | 70 |
| 20 | 67 | 72 | 75 | 200 |
| 100 | 74 | 80 | 119 | Not clotted |
| 500 | 85 | 113 | | Not clotted |

Further validation of "NASP" activity was demonstrated by evaluation of three compounds in an APTT clotting assay with Hem-A plasma. Concentrations producing approximately 50% prolongation in clotting time were 10- or 100- or >500-fold higher for fucoidan, PPS, and NAH, respectively, than for heparin (see FIG. 3).

EXAMPLE 5

Inhibition of TFPI Activity by NASPs

A. Preincubation of TFPI with NASPs Prior to Addition to Plasma

Inhibition of TFPI activity by NASPs was assessed in dPT clotting assays with normal or hemophilic plasma and added recombinant TFPI. Diluted recombinant TFPI was preincubated with NASPs for 5 minutes at room temperature before plasma was added. After addition of plasma, the mixture was incubated for an additional 25 minutes followed by dPT initiation. The results for assays performed in Hem-A plasma are shown in Table 6 and FIG. 4.

TABLE 6

NASP Inhibition of TFPI Activity in Hem-A Plasma

| NASP Concentration (nM) | Fucoidan clotting time (sec) | PPS clotting time (sec) | NAH clotting time (sec) |
|---|---|---|---|
| 500 | 75 | 74 | 84 |
| 100 | 46 | 57 | 99 |
| 20 | 54 | 55 | 141 |
| 4 | 72 | 91 | 160 |
| 0.8 | 108 | 111 | 158 |
| 0.16 | 130 | 158 | 144 |

Clotting time of Hem-A plasma alone is 44 seconds.
Clotting time of Hem-A plasma + TFPI is 151 seconds.

Figure 4:
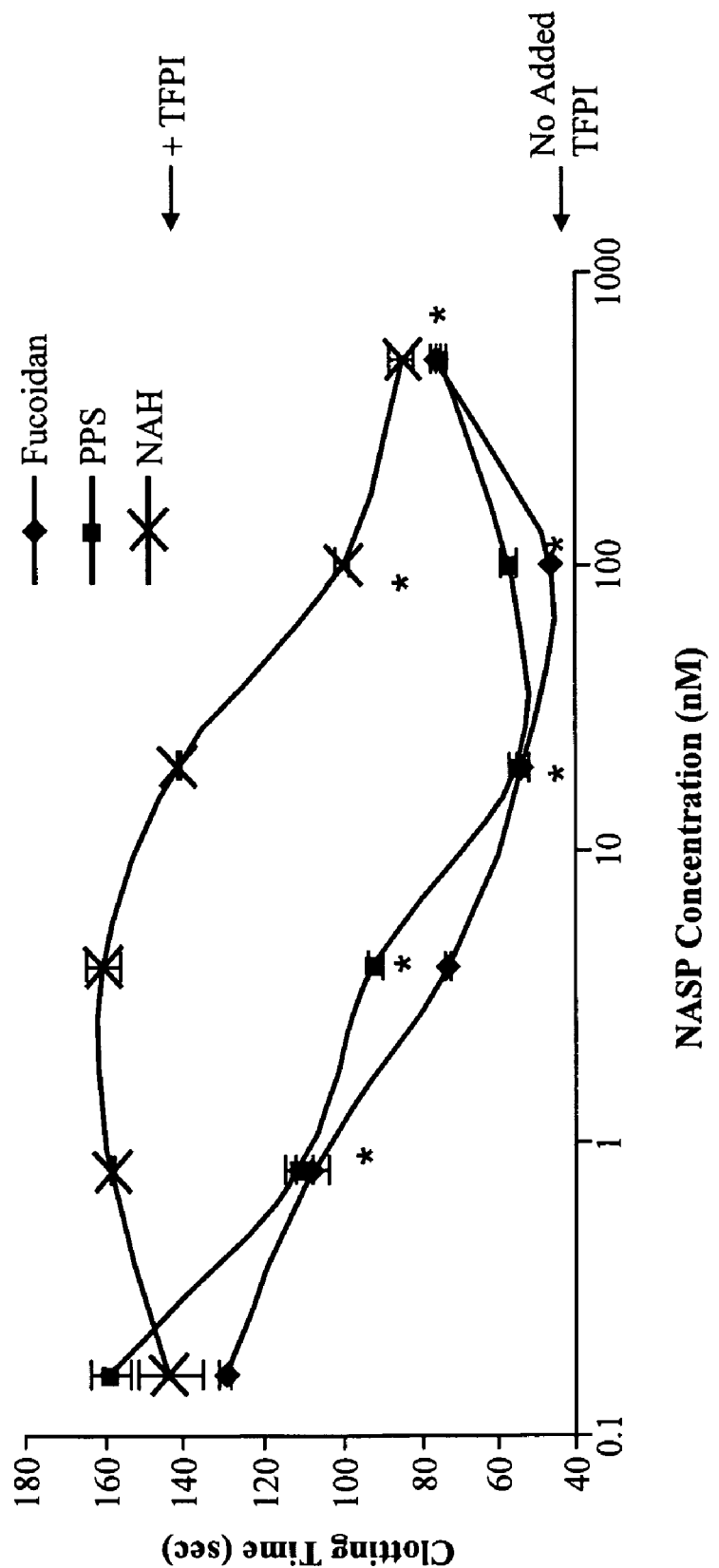
FIG. 4 shows that NASPs, including NAH, PPS, and fucoidan accelerate clotting of Hem-A plasma containing recombinant TFPI. NASPs were briefly preincubated with TFPI prior to addition to plasma. Clotting times were determined using the dPT assay. A plot of clotting time (seconds) versus NASP concentration (nM) is shown. Data points shown are mean values from duplicate measurements. NASP inhibition of TFPI activity resulted in reduced plasma clotting times.

TFPI at a final concentration of approximately 0.5 µg/ml prolonged the clotting time of plasma from approximately 40 seconds to 100-200 seconds depending on the experiment and source of human plasma. If TFPI activity were inhibited by sulfated polysaccharides, then a shortening of clotting time should be observed in the presence of NASPs (see Nordfang et al. (1991) Thromb. Haemost. 66(4):464-467). As shown in FIG. 4, addition of fucoidan and PPS at concentrations greater than 1 nM significantly accelerated clotting of Hem-A plasma containing TFPI. In contrast, NAH required concentrations of approximately 100 nM to shorten clotting time, and heparin (not shown) only prolonged clotting times. Importantly, at optimal concentrations of PPS or fucoidan, the clotting time was shortened to the no TFPI, or vehicle control levels, or slightly below, and the breadth of neutralization of TFPI effect spanned at least a 100-fold range (e.g., 5 to 500 nM).

Figure 5:
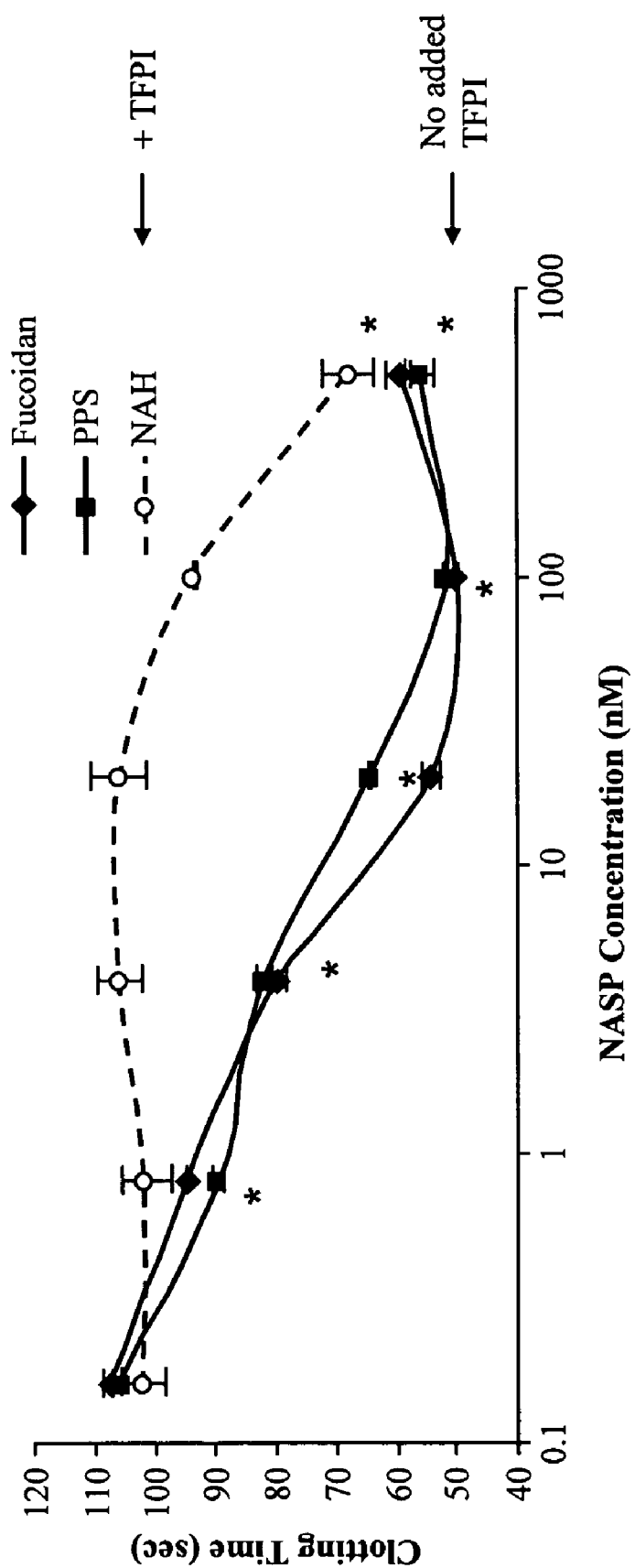
FIG. 5 shows that NASPs, including NAH, PPS, and fucoidan accelerate clotting of hemophilia B (Hem-B) plasma containing recombinant TFPI. NASPs were briefly preincubated with TFPI prior to addition to plasma. Clotting times were determined using the dPT assay. A plot of clotting time (seconds) versus NASP concentration (nM) is shown. Data points shown are mean values from duplicate measurements. NASP inhibition of TFPI activity resulted in reduced plasma clotting times.

The acceleration of plasma clotting by the NASPs in the presence of TFPI was also tested in Hem-B and normal plasma. The results for assays performed in Hem-B plasma are shown in Table 7 and FIG. 5.

TABLE 7

NASP Inhibition of TFPI Activity in Hem-B Plasma

| NASP Concentration (nM) | Fucoidan clotting time (sec) | PPS clotting time (sec) | NAH clotting time (sec) |
|---|---|---|---|
| 500 | 60 | 56 | 68 |
| 100 | 50 | 52 | 94 |
| 20 | 54 | 65 | 106 |
| 4 | 80 | 82 | 106 |
| 0.8 | 95 | 90 | 101 |
| 0.16 | 108 | 106 | 102 |

Clotting time of Hem-B alone, no TFPI: 46 seconds.
Clotting time of Hem-B + TFPI: 101 seconds.

The acceleration of plasma clotting by the NASPs, presumably by inhibition of TFPI activity, was similarly demonstrated in Hem B plasma (Table 7 and FIG. 5) and normal human plasma (data not shown). The rank order of potency between NASPs was identical to the studies with Hem A plasma and the concentration-response profile was nearly identical.

B. Inhibition of TFPI Activity with No Preincubation of TFPI with NASPs

Experiments were repeated without a preincubation of the sulfated polysaccharides with TFPI prior to exposure to plasma. To extend the stringency of the test for NASP inhibition of TFPI activity, TFPI was added to the plasma before the NASP was added. The results are shown in Table 8 and FIG. 6.

TABLE 8

Inhibition of TFPI by NAH and PPS in Hem-A Plasma Without Preincubation

| NASP Concentration (nM) | NAH clotting time (sec) | PPS clotting time (sec) | Fucoidan clotting time (sec) |
|---|---|---|---|
| 500 | 89 | 73 | 90 |
| 100 | 125 | 76 | 54 |
| 20 | 184 | 81 | 59 |
| 4 | 180 | 156 | 78 |
| 0.8 | 165 | 192 | 210 |

HemA + TFPI: 183 seconds
Hem-A alone, no TFPI: 45 seconds

Figure 6:
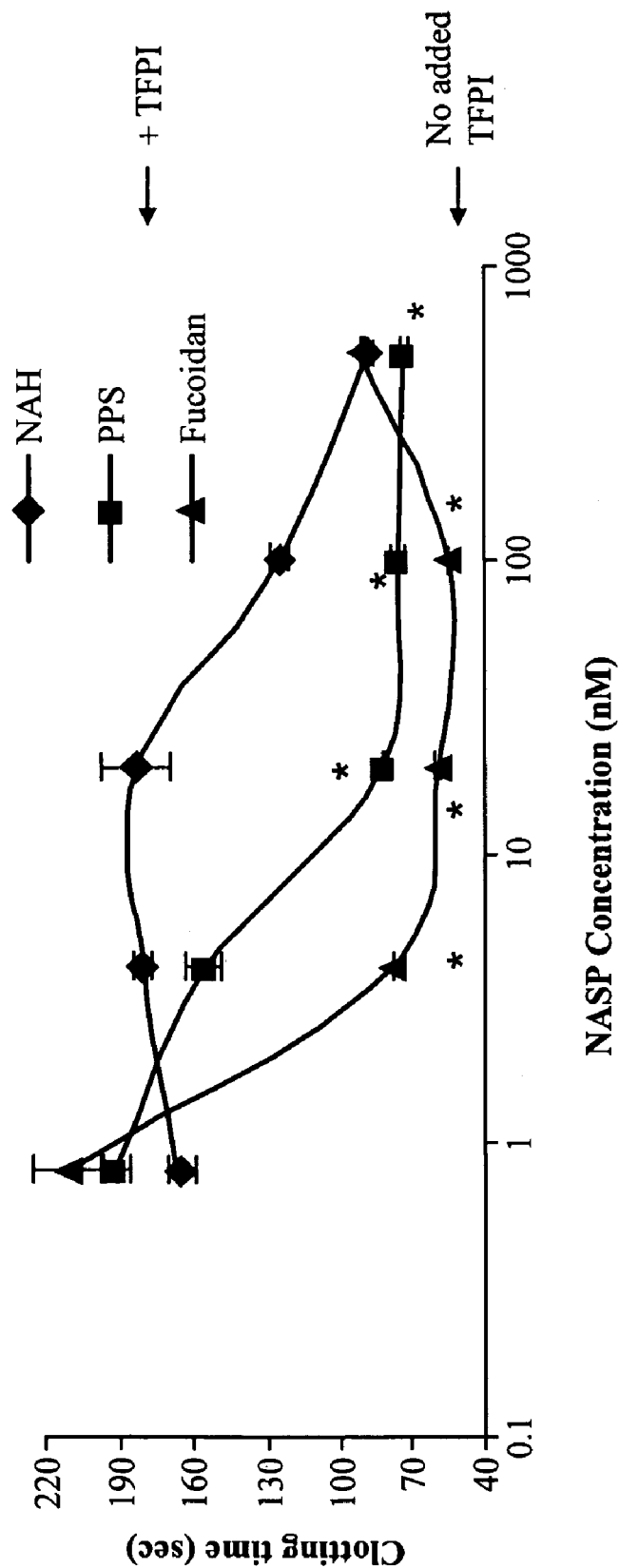
FIG. 6 shows that NAH, PPS, and fucoidan accelerate clotting of Hem-A plasma containing TFPI without preincubation of TFPI with NASPs prior to introduction of TFPI into plasma. A plot of clotting time (seconds) versus NASP concentration (nM) is shown. Clotting times were determined using the dPT assay. Data points shown are mean values from duplicate measurements.

As depicted in FIG. 6, the NASPs clearly demonstrated the same property of clotting time acceleration in Hem A plasma with nearly identical dose-response profiles as in the preincubation studies (FIG. 4). Interestingly, fucoidan was most potent and the concentration window for significant clotting acceleration was greater than 100-fold. These studies therefore established that certain NASPs such as PPS and fucoidan could exhibit TFPI neutralizing activity, and that such efficacy was demonstrated across a very broad range of concentrations wherein net anticoagulation was not observed.

EXAMPLE 6

Improvement in Hemophilic Plasma Coagulation by NASPs in the Absence of TFPI Supplementation The ability of NASPs to accelerate clotting of factor-deficient plasma in the absence of TFPI supplementation was also tested in dPT assays. A procoagulant response, if observed, may be related to neutralization of endogenous TFPI activity, which is present in human plasma at approximately 100 ng/ml (Nordfang et al., supra), largely associated with lipoprotein or platelets (Broze et al. (1992) Semin. Hematol. 29:159-169; Broze et al. (2003) J. Thromb. Haemost. 1:1671-1675).

A. Acceleration of Clotting in Hem-A Plasma in Absence of Exogenous TFPI

Figure 7:
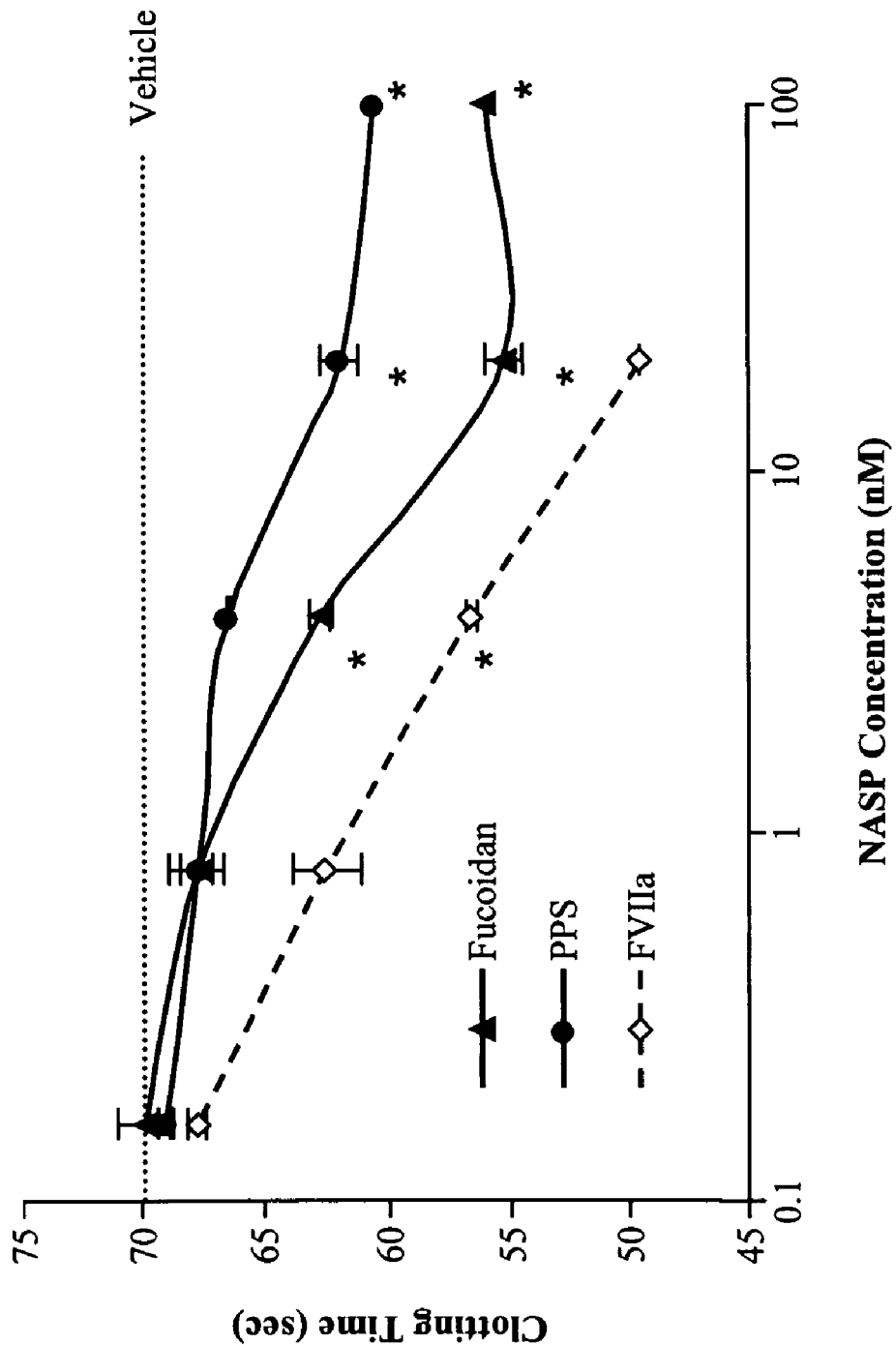
FIG. 7 shows that PPS and fucoidan accelerate clotting of Hem-A plasma in the absence of exogenous TFPI supplementation. The dose-response of NASPs is compared to a positive control, factor VIIa, for amplification of extrinsic pathway activation.

The ability of NASPs to accelerate clotting of Hem-A plasma in the absence of exogenous TFPI was tested. Fucoidan or PPS were titrated into Hem A plasma and dPT assays were performed. Additionally, the dose-response to factor VIIa was analyzed as a positive control for amplifying extrinsic pathway activation. The results are shown in FIG. 7 and Table 9.

TABLE 9

Acceleration of Hem-A Plasma Clotting In Absence of Exogenous TFPI

| NASP Concentration (nM) | Fucoidan clotting time (sec) | PPS clotting time (sec) | FVIIa clotting time (sec) |
|---|---|---|---|
| 100 | 56 | 60 | |
| 20 | 55 | 62 | 49 |
| 4 | 63 | 66 | 56 |

TABLE 9-continued

Acceleration of Hem-A Plasma Clotting In Absence of Exogenous TFPI

| NASP Concentration (nM) | Fucoidan clotting time (sec) | PPS clotting time (sec) | FVIIa clotting time (sec) |
|---|---|---|---|
| 0.8 | 68 | 68 | 62 |
| 0.16 | 70 | 69 | 68 |

Clotting time of Hem-A alone, no NASP: 69 seconds

Fucoidan and PPS both significantly accelerated the clotting time in a dose-dependent fashion with fucoidan exhibiting the best potency and maximal efficacy. As in other studies, there was a window of procoagulant effect that, in the case of fucoidan, ranged from approximately 5 nM to >100 nM. Note in FIG. 7 that while the response curve begins to deflect upwards at concentrations of fucoidan >100 nM, clotting is still accelerated relative to the vehicle control, and fucoidan is hence procoagulant. While the shortening of clotting time from about 70 seconds to 55 seconds at 20 nM fucoidan is not a large margin, NAH had no activity. Such acceleration has been observed previously with procoagulant factors like FVIIa and thrombin. Accordingly, FVIIa addition to 20 nM accelerated clotting times by approximately 20 seconds, which was greater than that of fucoidan (FIG. 7). However, it is interesting to note that 20 nM fucoidan performed comparably to a pharmacological concentration of 5 nM FVIIa.

B. Acceleration of Clotting in Hem-B plasma and FVII-Deficient Plasma in Absence of Exogenous TFPI Evaluation of the apparent procoagulant activity of NASPs was extended to other human bleeding disorders by testing NASP activity in Hem B plasma and FVII-deficient plasma. Similar results to those shown for Hem-A plasma were observed for Hem-B plasma (data not shown).

Figure 8:
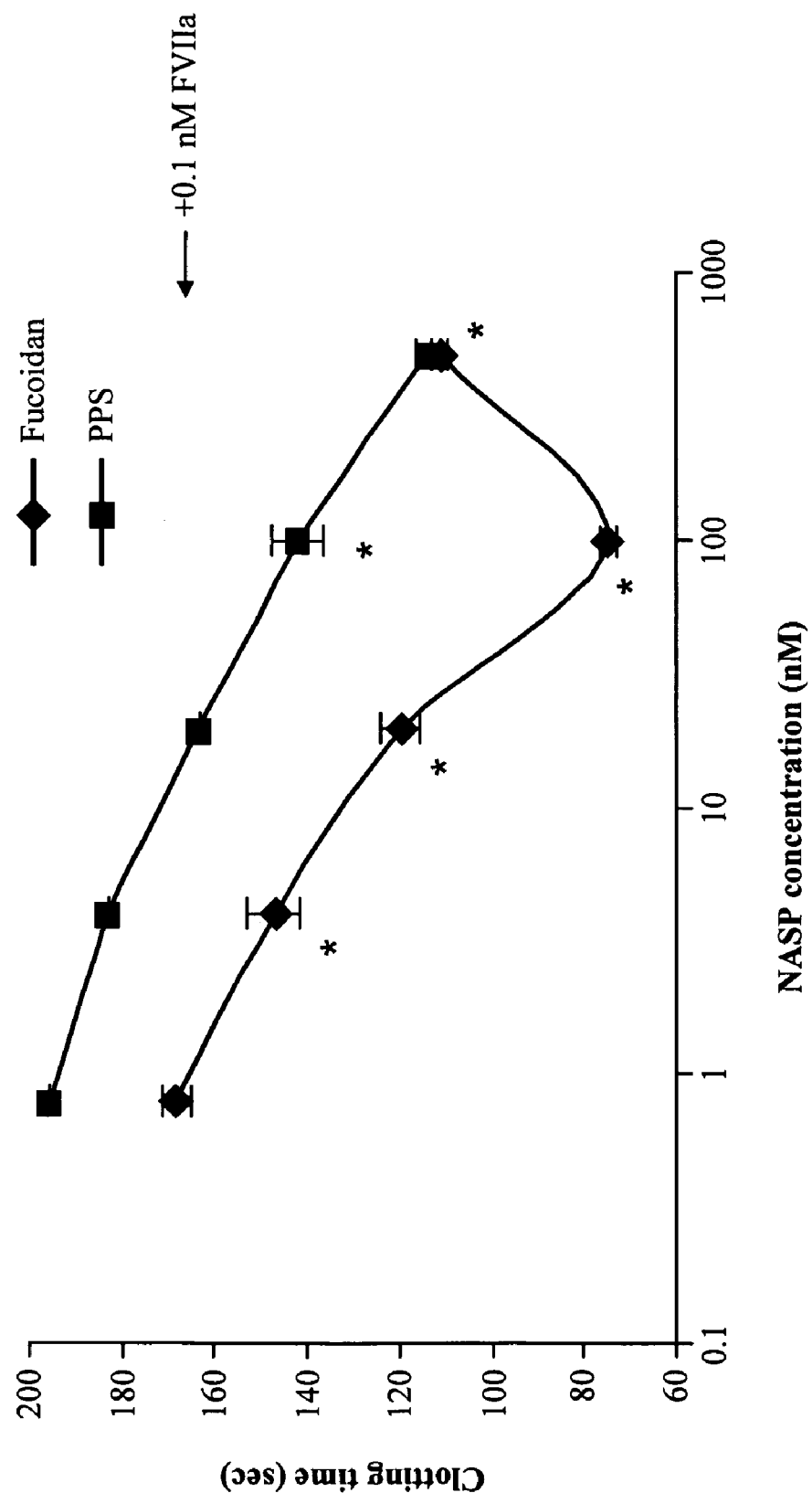
FIG. 8 shows that fucoidan and PPS accelerate clotting of factor VII-deficient plasma in dPT assays. Clotting time was measured following preincubation of factor VII-deficient plasma with varying concentrations of fucoidan or PPS.

Regulation of clotting in Factor VII-deficient plasma was also evaluated in dPT assays. As expected, FVII-deficient plasma failed to clot within 300 seconds without FVIIa reconstitution. Addition of FVIIa to approximately 0.1 nM restored the clotting time to about 150 seconds (data not shown). Such a variation in clotting time shown in the dPT assay mimics some forms of human factor VII-deficiency. Titration of fucoidan and PPS into FVII-deficient plasma accelerated clotting times. The results are shown in FIG. 8 and Table 10.

TABLE 10

Acceleration of Factor VII-Deficient Plasma Clotting In Absence of Exogenous TFPI

| NASP Concentration (nM) | Fucoidan clotting time (sec) | PPS clotting time (sec) |
|---|---|---|
| 500 | 111 | 113 |
| 100 | 74 | 142 |
| 20 | 120 | 159 |
| 4 | 147 | 181 |
| 0.8 | 168 | 198 |

Clotting time with no NASP, no FVIIa: >300 seconds
Clotting time with no NASP, +0.1 nM FVIIa: 173 seconds As shown in FIG. 8, titration of fucoidan and PPS accelerated clotting of Factor VII-deficient plasma and, as observed with Hem A plasma, fucoidan was significantly more potent and effective than PPS. Once again, the therapeutic window was broad; in the case of fucoidan, substantial acceleration of clotting was observed with concentrations ranging from approximately 10 nM to 500 nM.

EXAMPLE 7

Improved Hemostasis of NASP-Treated Mice

Hem A or Hem B mice were treated with PPS and fucoidan to assess potential improvement of hemostasis in vivo. NASPs were injected subcutaneously as frequent dosing is reasonably well tolerated in hemophilic mice and bioavailability from this route for various sulfated polysaccharides has been previously established (MacGregor et al. (1985) Thromb. Haemost. 53:411-414; Millet et al. (1999) Thromb. Haemost. 81:391-395). PPS and fucoidan half-lives may be as short as 1-2 hours. Therefore, a twice daily dosing regimen was adopted. Initial studies indicated that dosing for several days was preferred over 1-2 days.

The effects of NASP treatment on coagulation regulation in the treated mice was evaluated based on several potential endpoints, including plasma isolation for dPT assays, blood sampling for whole blood clotting time (WBCT) assays, acute bleeding times, and longer-term survival following tail snip or transverse incision (Broze et al. (2001) Thromb. Haemost. 85:747-748). The results from 5-day in vivo studies with PPS and fucoidan are summarized in Tables 11-13.

A. PPS Efficacy in Hem-A and Hem-B Mice

The efficacy of PPS in improving clotting in Hem-A and Hem-B mice was tested. Hem-A and Hem-B male or female mice were administered PPS at a dose of 0.02, 0.06, or 0.2 mg/kg or saline vehicle subcutaneously twice daily for 5 days. On the morning of the fifth day after dosing, the tail was clipped 1 cm from the tip, and behavior and survival were monitored for the next 20-24 hours. The results are shown in Table 11.

TABLE 11

Improved Hemostasis in PPS-Treated Hemophilic Mice

| Hemophilia | Treatment Group | n/group | % Survival (20 hours post-cut) |
|---|---|---|---|
| A (FVIII-deficient) | Vehicle control | 8 | 25 |
| | 0.02 mg/kg | 5 | 20 |
| | 0.06 mg/kg | 9 | 44[#] |
| | 0.2 mg/kg | 5 | 40 |
| B (FIX-deficient) | Vehicle control | 8 | 25 |
| | 0.06 mg/kg | 9 | 44[#] |

Mice were randomized and dosed subcutaneously with indicated agent twice daily for 4.5 days followed by tail cut (t = 0).
[#]p = 0.07 vs. vehicle Treatment of Hem-A mice with PPS at 0.06 mg/kg showed a nearly two-fold improvement in survival, but the result was not statistically significant ($0.05 < p < 0.1$) (Table 11). Therapeutic benefit was further supported by visual observations by technical staff blinded to treatment group who observed more normal behavior (less lethargy and hunching) and less extensive bleeding in the mid and high dose animals relative to the vehicle controls. Likewise, subsequent treatment of Hem-B mice with the more effective dose of 0.06 mg/kg subcutaneously twice daily yielded an identical result as that observed in the FVIII-deficient mice.

The efficacy of PPS in improving clotting in Hem-B mice was further tested in dPT assays. All mice were bled prior to the study to establish baseline (pretest) clotting times. Mice (14 weeks old) were treated subcutaneously twice a day with PPS for 4.5 days at the following doses: 2, 0.3 and 0.06 mg/kg in a volume of 250 μl. Mice were bled after 4.5 days, and clotting times were determined from collected blood samples. The results are shown in Table 12.

TABLE 12

Clotting for Hem-B Mice Treated with PPS NASPs Improve dPT

| Group (mg/kg) | Individual clotting times at 4.5 days (min) | Mean clotting time at 4.5 days (min) |
|---|---|---|
| 0.06 | 44 | 37 |
| | 42 | |
| | 26 | |
| 0.3 | 43 | 38 |
| | 31 | |
| | 39 | |
| 2.0 | 42 | 44 |
| | 45 | |
| | 44 | |

Naïve Hem-B have dPT ranging from 44-50 seconds.

B. Fucoidan Efficacy in Hem-A Mice

Given the improved potency and magnitude of efficacy of fucoidan relative to PPS in some of the clotting assays described above, additional studies were performed in Hem-A mice with fucoidan. In the first study with fucoidan, nearly the same regimen as described for PPS was adopted, but with slightly different dose levels. Hem-A male mice were administered fucoidan at a dose of 0.1 or 1.0 mg/kg or saline subcutaneously twice daily for 4 days. On the morning of the 5th day, mice received a doubled dose of fucoidan prior to the bleeding test. Survival and animal behavior were evaluated for mice treated with fucoidan compared to vehicle controls.

In a second study with fucoidan, combination therapy potential with factor VIII was evaluated. This study was performed as described above, except on the morning of the fifth day, mice received an intravenous bolus dose of 53 mU/mouse FVIII (about 1.25% of the normal level of FVIII) in a tail vein far up near the body. As before, the lateral tail vein, and not the artery, was transected 2 hours later at the region corresponding to a diameter of about 2.7 mm. In these fucoidan studies, the tail vein transection modification was utilized as it was found to more accurately assess hemostasis and its regulation (Broze et al. (2001) Thromb. Haemost. 85:747-748). Survival and clinical observations were recorded for 20-24 hours. The results are shown in Table 13.

TABLE 13

Efficacy of Fucoidan and Combination Fucoidan + FVIII in Hemophila A Mice

| | | % Survival | |
|---|---|---|---|
| Treatment Group | n/group | 9 hr | 20 hr |
| Vehicle control | 14 | 21 | 7 |
| Fucoidan (0.1 mg/kg) | 13 | 61* | 38[+] |
| Factor VIII (1.25% reconstitution) | 7 | 57* | 57* |
| Fucoidan + FVIII | 7 | 86* | 86*[#] |

Mice were randomized and dosed subcutaneously with vehicle or NASP twice daily for 4.5 days followed by tail vein incision (t = 0). Where indicated, FVIII was administered 2 hours prior to tail cut. Note that 1% FVIII reconstitution yields ~10% survival whereas 2% FVIII reconstitution provides ~100% survival in these mice.
*p < 0.05 vs. vehicle
[+]p = 0.06 vs. vehicle
[#]p = 0.06 vs. fucoidan In the first study, treatment of mice with fucoidan at a dose of 0.1 mg/kg appeared to be more efficacious than treatment at a dose of 1.0 mg/kg (survival at about 10 hours was 1/6 for vehicle, 4/6 for 0.1 mg/kg, and 3/6 for 1.0 mg/kg). Hence, the second study was performed with fucoidan at a dose of 0.1 mg/kg.

As indicated in the top two rows of Table 13, fucoidan treatment of Hem A mice significantly improved bleeding survival. Animal behavior, as described above, was more normal in all the fucoidan-treated mice during the first 8-10 hours post-incision, and was clearly improved long-term in nearly half the animals.

Combination therapy potential was preliminarily assessed by treating mice with FVIII+/–fucoidan (Table 13). A preliminary dose-guiding study with FVIII administration alone to Hem A mice two hours prior to tail incision indicated a very steep dose-response relationship for survival. ReFacto® administration to 1% of normal yielded about 10% survival, whereas dosing to 2% of normal yielded about 100% survival (data not shown). Accordingly, a dose of 1.25% FVIII reconstitution was selected to give approximately 50% survival. Notably, the percent survival in the fucoidan+FVIII treatment group was consistently higher than either fucoidan or FVIII alone. Thus, the results of the PPS and fucoidan studies indicate that hemostasis is improved in animals models of hemophilia following select NASP administration.

CONCLUSION

A series of studies were undertaken to test NASPs for improvement of clotting in ex vivo and in vivo hemophilia models. Sulfated polysaccharides were identified with substantially reduced anticoagulant properties relative to heparin. A subset of those NASPs, namely fucoidan and PPS, were shown to potently inhibit the activity of TFPI, the predominant downregulator of the extrinsic pathway of blood coagulation. Fucoidan and PPS improved the dilute prothrombin clotting times of human plasma deficient in factors VII, VIII, or IX. Therapeutic benefit of fucoidan or PPS treatment in vivo was apparent from bleeding tests of hemophilic mice.

Both PPS and fucoidan may exhibit anticoagulant activity at higher concentrations, likely as a result of heparin cofactor II interaction (Church et al. (1989) J. Biol. Chem. 264:3618-3623; Giedrojc et al. (1999) J. Cardiovasc. Pharmacol. 34:340-345). PPS administered subcutaneously to rats requires doses >5 mg/kg to prolong clotting (Giedrojc et al., supra), and fucoidan seems well-tolerated in rabbits even when given intravenously at 10 mg/kg (Granert et al. (1999) Infect. Immun. 67:2071-2074). Hence, the current results show that hemostasis is improved at doses $\leq$0.1 mg/kg in hemophilic rodents. Dose levels that improved hemostasis in vivo were lower than those causing other reported effects (Toida et al. (2003) Trends in Glycoscience and Glycotechnology 15:29-46; Luyt et al. (2003) J. Pharmacol. Exp. Ther. 305:24-30; Berteau et al. (2003) Glycobiology 13:29R-40R; Granert et al., supra; and Sweeney et al. (2002) Blood 99:44-51).

Without being bound by a particular theory, NASP inhibition of TFPI may account in part for the observed improvements in coagulation ex vivo and in vivo. Neutralization of TFPI by antibodies has been shown to improve hemostasis in a rabbit Hem A model and to accelerate clotting of human hemophilic plasma (Nordfang et al., supra; Welsch et al., supra; and Erhardtsen et al. (1995) Blood Coagul. Fibrinolysis 6:388-394). In the current studies, only compounds inhibiting TFPI activity also reduced clotting times in the hemophilic plasma dPT assays. Additionally, fucoidan exhibited better potency and perhaps greater maximal effect compared to PPS in the dPT clotting test when the TFPI was first mixed into plasma to best mimic the natural setting. Likewise, fucoidan treatment of mice yielded somewhat better efficacy than PPS although undefined relative pharmacokinetics may have influenced the bleeding outcomes.

It is noteworthy that such behavior was not apparent with all tested NASPs. For example, NAH exhibited only weak TFPI-neutralizing activity (FIGS. 4-6) and did not accelerate hemophilic plasma clotting times in the absence of TFPI addition (data not shown). Moreover, three NASPs which failed to show inherent anticoagulant activity at concentrations up to 5000 nM (FIG. 2; De-N—S-AH, De-N—SH, and NA-De-O—SH) did not exhibit any TFPI-neutralizing activity and likewise failed to accelerate clotting times in Hem A plasma (data not shown).

The magnitude of improved hemostasis observed with NASPs appears to be clinically relevant. Improved clotting times of Hem A plasma at optimal fucoidan concentrations were comparable to FVIIa supplementation at approximately 5 nM (Example 6) which has proven effective in normalizing hemostasis in patients (Bishop et al. (2004) Nat. Rev. Drug Discov. 3:684-694; Carcao et al. (2004) Blood Rev. 18:101-113; Roberts et al. (2004) Anesthesiology 100:722-730; Lee et al. (2004) Int. Anesthesiol. Clin. 42:59-76; and Brummel et al. (2004) J. Thromb. Haemost. 2:1735-1744). In addition, survival benefit with NASP treatment in mice was significant (Example 7). Fucoidan acceleration of clotting in dPT assays is more pronounced with human hemophilic plasma than mouse plasma (data not shown).

An obvious consideration regarding potential clinical development of a NASP for bleeding disorders would be therapeutic index. Specifically, index between improved hemostasis and the transition to anti-coagulation. From the clotting assay results for compounds such as PPS or fucoidan in human plasma, the margin between anti-TFPI or accelerated dPT clotting "activity" and loss of such efficacy and onset of net anticoagulation would appear to be $\geq$50-fold. As mentioned above for the mouse studies, the index would appear in mice to be at least ten-fold. Furthermore, as a class, heparin-like sulfated polysaccharides are generally well-tolerated.

In summary, systemic administration of select NASPs may represent a unique approach for regulating hemostasis in bleeding disorders. Pentosan polysulfate and fucoidan, in particular, inhibited TFPI activity and improved clotting of human factor VII-, VIII-, and IX-deficient plasmas. Thus, NASP treatment improved hemostasis and may represent a relatively low-cost, safe, and convenient alternative or supplement to current coagulation factor therapies.

While the preferred embodiments of the invention have been illustrated and described, it will be appreciated that various changes can be made therein without departing from the spirit and scope of the invention.

The invention claimed is:

1. A method for treating a subject for a bleeding disorder, the method comprising administering a therapeutically effective amount of a composition comprising a procoagulant amount of a non-anticoagulant sulfated polysaccharide (NASP) selected from the group consisting of:
pentosan polysulfate (PPS); and
a modified heparin selected from the group consisting of N-acetyl-heparin (NAH), N-acetyl-de-O-sulfated-heparin (NA-de-o-SH), de-N-sulfated-heparin (De-NSH), and de-N-sulfated-acetylated-heparin (De-NSAH), each having a molecular weight in the range of 10,000 Da to 1,000,000 Da;

and combinations thereof, to said subject;

wherein the NASP is administered at a dosage of about 0.01 mg/kg to about 100 mg/kg, and the bleeding disorder is selected from the group consisting of a chronic or acute bleeding disorder, a congenital coagulation disorder caused by a blood factor deficiency, and an acquired coagulation disorder.

2. The method according to claim 1, wherein the composition further comprises one or more factors selected from the group consisting of factor XI, factor XII, prekallikrein, high molecular weight kininogen (HMWK), factor V, factor VII, factor VIII, factor IX, factor X, factor XIII, factor II, and von Willebrands factor, tissue factor, factor VIIa, factor Va, and factor Xa, factor IXa, factor XIa, factor XIIa, and VIIIa.

3. The method of claim 1, wherein the bleeding disorder is a blood factor deficiency of one or more factors selected from the group consisting of factor V, factor VII, factor VIII, factor IX, factor X, factor XI, factor XII, factor XIII, and von Willebrand factor; a fibrinogen disorder; a prothrombin disorder; or a platelet dysfunction.

4. The method of claim 1, wherein the bleeding disorder is caused by prior administration of an anticoagulant or surgery or other invasive procedure.

5. The method of claim 1, further comprising administering an agent selected from the group consisting of a procoagulant, an activator of the intrinsic coagulation pathway, an activator of the extrinsic coagulation pathway, and a second NASP.

6. The method of claim 5, wherein the activator of the intrinsic coagulation pathway is selected from the group consisting of factor Xa, factor IXa, factor XIa, factor XIIa, and VIIIa, prekallekrein, and high-molecular weight kininogen.

7. The method of claim 5, wherein the activator of the extrinsic coagulation pathway is selected from the group consisting of tissue factor, factor VIIa, factor Va, and factor Xa.

8. The method of claim 1, further comprising administering one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor.

9. The method of claim 4, wherein the anticoagulant is selected from the group consisting of heparin, a coumarin derivative, such as warfarin or dicumarol, tissue factor pathway inhibitor (TFPI), antithrombin III, lupus anticoagulant, nematode anticoagulant peptide (NAPc2), active-site blocked factor VIIa (factor VIIai), factor IXa inhibitors, factor Xa inhibitors, inhibitors of factors Va and VIIIa, thrombin inhibitors, and an antibody that binds a clotting factor.

10. The method of claim 9, wherein the anticoagulant is an antibody that binds a clotting factor selected from the group consisting of Factor V, Factor VII, Factor VIII, Factor IX, Factor X, Factor XIII, Factor II, Factor XI, Factor XII, von Willebrands factor, prekallikrein, and high molecular weight kininogen (HMWK).

11. The method according to claim 1, wherein the NASP is PPS.

12. The method according to claim 1, wherein the NASP is NAH.

13. The method according to claim 1, wherein the NASP is NA-de-o-SH.

14. The method according to claim 1, wherein the NASP is De-NSH.

15. The method according to claim 1, wherein the NASP is De-NSAH.

* * * * *

UNITED STATES PATENT AND TRADEMARK OFFICE
CERTIFICATE OF CORRECTION

Page 1 of 1

PATENT NO.      : 7,829,549 B2
APPLICATION NO. : 12/386026
DATED           : November 9, 2010
INVENTOR(S)     : Kirk W. Johnson It is certified that error appears in the above-identified patent and that said Letters Patent is hereby corrected as shown below:

Col. 33 (Originally Claim 13), line 16, replace the word "Vila" with "VIIa"

Col. 34 (Originally Claim 22), line 16, replace the word "Vila" with "VIIa"

Signed and Sealed this
Fifth Day of April, 2011

David J. Kappos
*Director of the United States Patent and Trademark Office*